US006861569B2

(12) United States Patent
Dahl et al.

(10) Patent No.: US 6,861,569 B2
(45) Date of Patent: Mar. 1, 2005

(54) PROCESSES FOR THE PURIFICATION OF HIGHER DIAMONDOIDS AND COMPOSITIONS COMPRISING SUCH DIAMONDOIDS

(75) Inventors: Jeremy E. Dahl, Palo Alto, CA (US); Robert M. Carlson, Petaluma, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 366 days.

(21) Appl. No.: 10/052,636

(22) Filed: Jan. 17, 2002

(65) Prior Publication Data

US 2002/0188163 A1 Dec. 12, 2002

Related U.S. Application Data

(63) Continuation-in-part of application No. 10/017,821, filed on Dec. 12, 2001.
(60) Provisional application No. 60/262,842, filed on Jan. 19, 2001.

(51) Int. Cl.[7] .............................. C07C 13/28; C07C 7/00
(52) U.S. Cl. ....................... 585/352; 585/21; 585/800; 585/803; 585/16; 585/802; 117/68; 117/69; 117/70
(58) Field of Search .......................... 585/803, 21, 16, 585/800, 352, 802; 117/68, 69, 70

(56) References Cited

U.S. PATENT DOCUMENTS

| | | | |
|---|---|---|---|
| 3,457,318 A | | 7/1969 | Capaldi |
| 3,832,332 A | | 8/1974 | Thompson |
| 4,952,748 A | | 8/1990 | Alexander |
| 4,952,749 A | | 8/1990 | Alexander |
| 4,952,757 A | | 8/1990 | Purcell et al. |
| 4,982,049 A | | 1/1991 | Alexander |
| 5,017,734 A | | 5/1991 | Baum |
| 5,019,665 A | | 5/1991 | Partridge |
| 5,245,104 A | | 9/1993 | Cullick |
| 5,268,513 A | | 12/1993 | Shen |
| 5,298,666 A | | 3/1994 | Shen |
| 5,306,851 A | * | 4/1994 | Wu et al. ............. 585/22 |
| 5,334,228 A | * | 8/1994 | Ashjian et al. ............. 44/347 |
| 5,347,063 A | | 9/1994 | Shen |
| 5,369,213 A | | 11/1994 | Shen |
| 5,380,947 A | | 1/1995 | Chen |
| 5,382,684 A | | 1/1995 | Moini |
| 5,394,733 A | | 3/1995 | Acholla |
| 5,397,488 A | | 3/1995 | Chen |
| 5,410,092 A | | 4/1995 | Shen |
| 5,414,189 A | * | 5/1995 | Chen et al. ............. 585/801 |
| 5,430,193 A | | 7/1995 | Shen |
| 5,461,184 A | | 10/1995 | Swanson |
| 5,498,812 A | | 3/1996 | Bradway |
| 5,576,355 A | | 11/1996 | Chen |
| 6,235,851 B1 | | 5/2001 | Ishii |

FOREIGN PATENT DOCUMENTS

| | | |
|---|---|---|
| EP | 0399851 B1 | 11/1996 |
| WO | WO 95/06019 | 3/1995 |
| WO | WO 95/11472 | 4/1995 |

OTHER PUBLICATIONS

Aczel, et al., "Stability of Adamantane and its Derivatives to Coal–liquefaction Conditions, and its implications toward the organic structure of Coal", *Fuel*, vol. 58, pp. 228–230, Mar. 1979.

Balaban, et al., Systemic Classification and Nomenclature of Diamond Hydrocarbons–1, *Tetrahedron*, 34, pp. 3599–3606, (1978), no month.

Badziag, P., et al., "Nanometre–sized Diamonds are More Stable than Graphite", *Nature*, vol. 343, pp. 244–245, and 517 (Jan. 1990).

Bagrii, Ye, et al., "Catalytic Breakdown of Paraffinic Hydrocarbons in the Presence of Adamantanes", *Petrol. Chem USSR*, vol. 30, No. 2, pp. 131–134, (1990), no month.

Chung, et al., Recent Development in High–Energy Density Liquid Fuels, *Energy and Fuels, 13*, pp. 641–649, (1999), no month.

Dahl, J., et al., Diamondoid Hydrocarbons as Indicators of Natural Oil Cracking, *Nature, 399*, pp. 54–57, (1999), no month.

Drexler, Eric K., *Nanosystems: Molecular Machinery Manufacturing and Computation*, John Wiley & Sons, pp. 238–249, (1992), no month.

Fort, Jr., et al., Adamantane: Consequences of the Diamondoid Structure, *Chem. Rev., 64*, pp. 277–300, (1964), no month.

Hala, V.S., et al., "Analyse Unds erwendung on Pyrolyseol", *Jahrgang*, pp. 85–87, (Feb. 1971) In German—English Abstract on p. 85, considered only to extent of abstract.

Landa, S., "Adamantane and Its Homologues", *Current Science*, Gangalore, India, Vo. 32, pp. 485–489 (1963), no month.

Lin, et al., Natural Ocurrence of Tetramantane ($C_{22}H_{36}$), Pentamantane ($C_{26}H_{32}$), and Hexamantane ($C_{30}H_{36}$) in a Deep Petroleum Reservoir, *Fuel, 74*:10, pp. 1512–1521, (1995), no month.

(List continued on next page.)

*Primary Examiner*—Elizabeth D. Wood
(74) *Attorney, Agent, or Firm*—Burns, Doane, Swecker, Mathis, L.L.P.

(57) ABSTRACT

Disclosed are processes for the recovery and purification of higher diamondoids from a hydrocarbonaceous feedstock. Specifically disclosed is a multi-step recovery process for obtaining diamondoid compositions enhanced in tetramantane components and other higher diamondoid components. Also disclosed are compositions comprising at least about 10 weight percent of non-ionized tetramantane components and other higher diamondoid components and at least about 0.5 weight percent of non-ionized pentamantane components and other higher diamondoid components based on the total weight of diamondoid components present.

21 Claims, 34 Drawing Sheets

OTHER PUBLICATIONS

McKervey, Synthetic Approaches to Large Diamondoid Hydrocarbonds, *Tetrahedron, 36*, pp. 971–992, (1980), no month.

Machacek, V., et al., "Let Od Objeveni Adamantanu", *Chemicke Listy/svazek*, pp. 753–761, (1982) Russian—English Abstract on p. 761, no month, considered only to extent of abstract.

Oya, A, et al., "Carbonization of Adamantanes to a Graphitizable Carbon", *Fuel*, vol. 60, pp. 667–669, (Aug. 1981).

Petrov, A., "Hydrocarbons of Adamantane Series as Indicies of Petroleum Catagenesis Process", *Advances in Organic Geo Chemistry*, $6^{th}$ International Meeting on Organic Geochemistry, pp. 517–522 (1973), no month.

Prusova, D., Liquid Chromatography of Adamantanes and Carbon Adsorbents, *J. Chrom*, 234, pp. 1–11, (1982), no month.

Rollman, L., et al., "Adamantanes From Petroleum, with Zeolites", American Chemical Study, $210^{th}$ ACS National Meeting, Abstract and paper, Aug. 20, 1995.

Sandia National Laboratories (2000), World's First Diamond Micromachines Created at Sandia, Press Release, (Feb. 22, 2000), www.Sandia.gov.

Schleyer, P., et al., "Nonacyclo [$11.7.1.1^{2.18}.0^{3.16}.0^{4.13}.0^{5.10}.0^{6.14}.0^{7.11}.0^{15.20}$]–Docosane, a Bastard Tetramantane", *J. of the Am. Chem. Soc.*, 90:8, letter to the editor, Aug. 28, 1968.

Shen, M., et al., Finite $T_d$ Symmetry Models for Diamond: From Adamantane to Superadamantane ($C_{35}H_{30}$), *J. Am., Chem. Soc.*, vol. 114, No. 2, pp 497–505, (1992), no month.

Supryadkina, NY, et al., "Catalytic Dealkylation of Alkyladamantanes", *Petrol. Chem., USSR*, vol. 28, No. 2, pp. 103–110, (1988), no month.

Tominaga, K., et al., "Next–generation Fine Chemicals Raw Material–Adamantane", *Chem Econ Eng. Review*, vol. 17, No. 10, pp. 23–29, (Oct. 1985).

Vodicka, L, et al., "High Performance Liquid Chromatography of Halogeno Derivatives of Adamantane and Diamantane", *J. Chrom*, 270, pp. 199–205, (1983), no month.

Wingerr, W., "G.c.–m.s. Analysis of Diamondoid Hydrocarbons in Smackover Petroleums", *Fuel*, vol. 71, pp. 37–42, (Jan. 1992).

* cited by examiner

* Atmospheric-Equivalent

First Column

Fraction 33

Second Column

GC Retention Time (min.)

*mirror plane*

[121] Tetramantane

[123] Tetramantane
(ENANTIOMERS)

[1(2)3] Tetramantane

GC/MS time (minutes)

* non-diamondoid impurities

FIG. 19
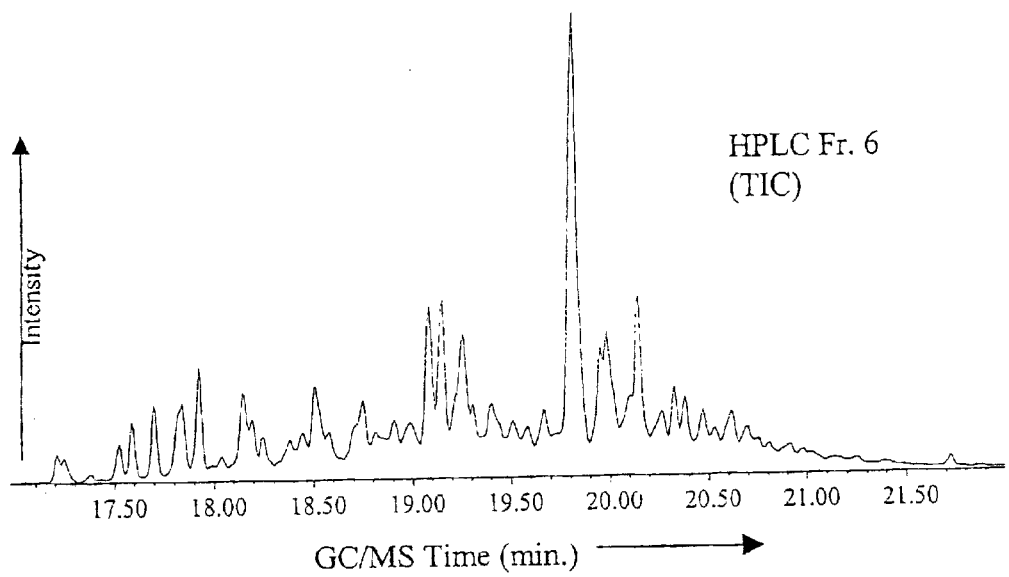
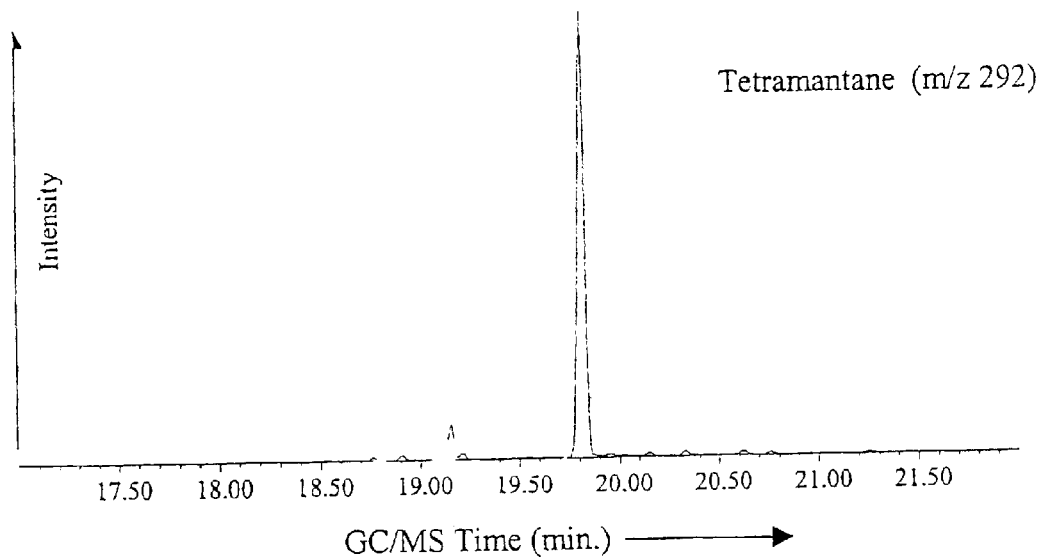

Time (min)

Time (min)

FIG. 27
𝒜.
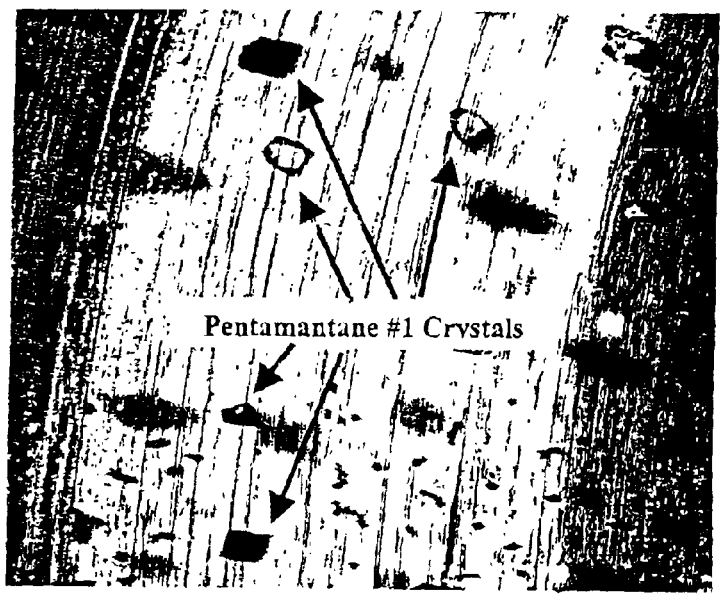
ℬ.
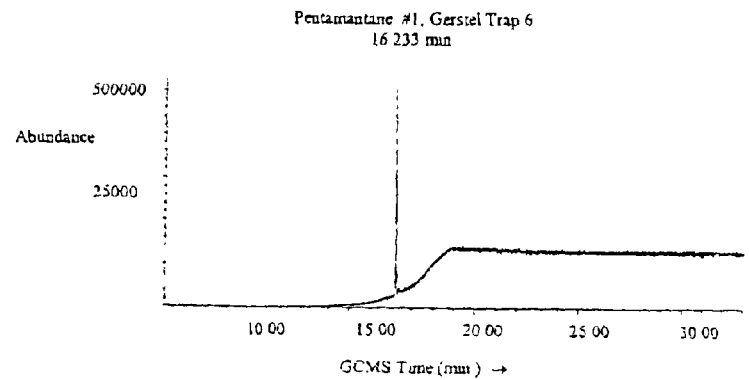
𝒞.
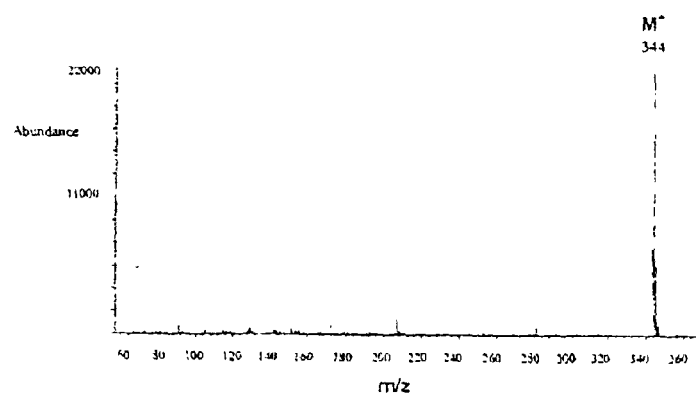

FIG. 28
A.
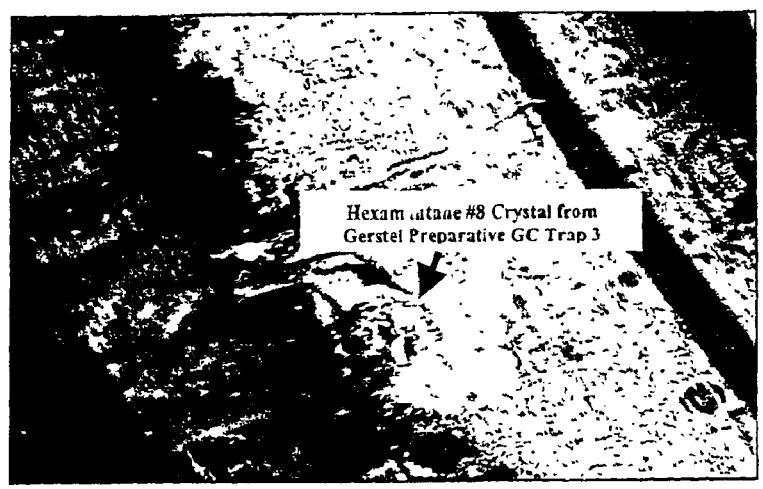
B.
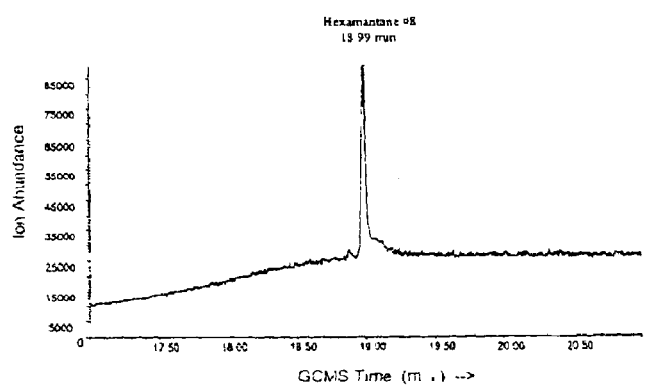
C.
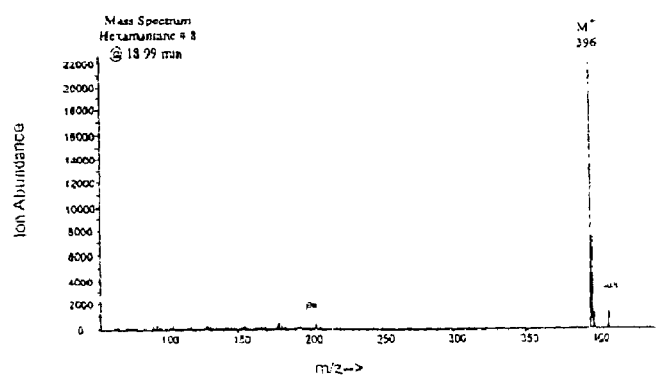

FIG. 29
A.
Heptamantane #1 Crystals
B.
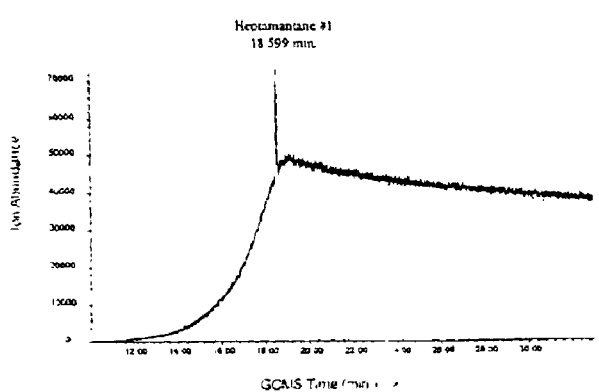
C.
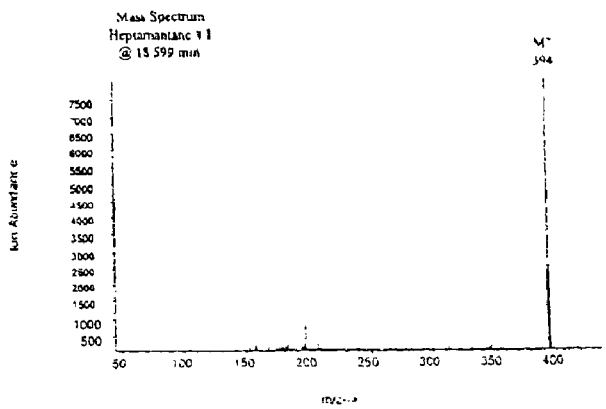

FIG. 30

| Number of Diamond Crystal Cage Units | Number of Molecular Formulae | Higher Diamondoid | Molecular Weights | | | | | | | |
|---|---|---|---|---|---|---|---|---|---|---|
| 4 | 1 | Tetramantane | 292 | | | | | | | |
| 5 | 2 | Pentamantane | 344 | 330 | | | | | | |
| 6 | 3 | Hexamantane | 396 | 382 | 342 | | | | | |
| 7 | 4 | Heptamantane | 448 | 434 | 394 | 420 | | | | |
| 8 | 5 | Octamantane | 500 | 486 | 446 | 420 | 432 | | | |
| 9 | 6 | Nonamantane | 552 | 538 | 498 | 524 | 484 | 444 | | |
| 10 | 7 | Decamantane | 604 | 590 | 550 | 576 | 536 | 496 | 456 | |
| 11 | 8 | Undecamantane | 656 | 642 | 602 | 628 | 588 | 548 | 508 | 534 |

FIG. 31

| Higher Diamondoid | 601-656 Fr.1 | 656-702 Fr.2 | 702-752 Fr.3 | 752-800 Fr.4 | 800-852 Fr.5 | 852-900 Fr.6 | 900-950 Fr.7 | 950-976 Fr.8 | 976-1000 Fr.9 | 1000-1026 Fr.10 |
|---|---|---|---|---|---|---|---|---|---|---|
| Tetramantanes | ▓ | ▓ | ▓ | ▓ | | | | | | |
| Pentamantanes | | ▓ | ▓ | ▓ | ▓ | | | | | |
| Cyclohexamantanes | | | ▓ | ▓ | ▓ | | | | | |
| Hexamantanes | | | | | ▓ | ▓ | | | | |
| Heptamantanes | | | | | | ▓ | ▓ | | | |
| Octamantanes | | | | | | ▓ | ▓ | ▓ | | |
| Nonamantanes | | | | | ▓ | ▓ | ▓ | ▓ | ▓ | ▓ |
| Decamantanes | | | | | | ▓ | ▓ | ▓ | ▓ | ▓ |
| Undecamantanes | | | | | | ▓ | ▓ | ▓ | ▓ | ▓ |

Distillation Cuts Made on Atmospheric Resid of Feedstock B (°F)

FIG. 32

Hexamantane

| CCS HPLC Fraction # | 1 | 2 | 3 | 4 | 5 | 6 | 7 | 8 | 9 | 10 | 11 | 12 | 13 | 14 | 15 | 16 | 17 | Fully Condensed Hexamantane | | | |
|---|---|---|---|---|---|---|---|---|---|---|---|---|---|---|---|---|---|---|---|---|---|
| 23 | | | | | | | | | | | | | | | | | | ■ | | | |
| 24 | | | | | | | | | | | | | | | | | | ■ | | | |
| 25 | | | | | | | | | | | | | | | | | | ■ | | | |
| 26 | | | | | | | | | | | | | | | | | | ■ | | | |
| 27 | | | | | | | | | | | | | | | | | | | | | |
| 28 | | . | | | | | | | | | | | | | | | | | | | |
| 29 | | x | | | | | | | | | | | | | | | | | Hex 2 | | |
| 30 | | . | | | | | | | | | | | | | | | | | | | |
| 31 | | . | | | | | | | | | | | | | | | | | | | |
| 32 | | . | | | | | | | | | | | | | | | | | | | |
| 33 | x | | | x | | | | | | | | | | | | | | | Hex 1 | Hex 4 | |
| 34 | | | | | | | | | | | | | | | | | | | | | |
| 35 | | | | | x | | | | | | ■ | | | | | | | | Hex 5 | | |
| 36 | | | | | | | ■ | | | | x | x | | | | | | | Hex 11 | Hex 13 | |
| 37 | | | | | | | x | | | | ■ | . | | | | | | | Hex 7 | | |
| 38 | | | | | | | ■ | . | ■ | | | . | | | | | | | | | |
| 39 | | | | | | | ■ | x | ■ | | | | | x | | | | | Hex 8 | Hex 9 | Hex 14 |
| 40 | | | | | | | ■ | . | | | | | | ■ | | | | | | | |
| 41 | | ■ | | | | | ■ | . | | | | | | ■ | | | | | | | |
| 42 | | ■ | | | | | ■ | | | | | | | | | | | | | | |
| 43 | | x | | | | | ■ | | | | | | | | ■ | | | | Hex 3 | | |
| 44 | | . | | | | | ■ | | | | | | | | ■ | x | | | Hex 12 | Hexa 16 | |
| 45 | | | | | | | ■ | | | | | | | | | x | ■ | | Hex 15 | | |
| 46 | | | | | | | ■ | | | | | | | | | | | | | | |
| 47 | | | | | | | ■ | | | | | | | | | | | | | | |
| 48 | | | | | | | | ■ | | | | | | | | | ■ | | Hex 10 | | |
| 49 | | | | | | | | ■ | | | | | | | | | ■ x | | Hex 17 | | |
| 50 | | | | | | | | ■ | | | | | | | | | ■ | | | | |
| 51 | - | - | | - | | - | - | | | | - | | | | - | | - | | | | |
| 52 | - | - | | - | | | - | | | - | | | | | | - | - | | | | |
| 61 | | | | | | | ■ | | | | | | | | | | | | | | |
| 62 | | | | | | | ■ | | | | | | | | | | | | | | |
| 63 | | | | | | | x | | | | | | | | | | | | Hex 6 | | |
| 64 | | | | | | | ■ | | | | | | | | | | | | | | |
| 65 | | | | | | | ■ | | | | | | | | | | | | | | |

FIG. 33

| Hypercarb HPLC Fraction # | 1 | 2 | 3 | 4 | 5 | 6 | 7 | 8 | 9 | 10 | 11 | 12 | 13 | 14 | 15 | 16 | 17 | Fully Condensed Hexamantane | |
|---|---|---|---|---|---|---|---|---|---|---|---|---|---|---|---|---|---|---|---|
| 1 | | | | | | | | | | | | | | | | | | | |
| 2 | | | | | | | | | | | | | | | | | | . | |
| 3 | | | | | | | | | | | | | | | | | | | |
| 4 | | | | | | | | | | | | | | | | | | ▓▓▓▓▓ | |
| 5 | | | | | | | | | | | | | | | | | | | |
| 26 | | | | | | | | | | | | | | | | | | | |
| 27 | | | | | | | | | | | | | x | | | | | | Hex 13 |
| 28 | | | | | | | | | | | | | | | | | | | |
| 29 | | | | | | | | | | | | | | x | | | | | Hex 14 |
| 30 | x | | | | | | | | | | | | | | | | | | Hex 1 |
| 31 | | | | | | | | | ■ | | | | | | | | | | Hex 10 |
| 32 | | | | | | | | | ■ | | | | | | | | | | Hex 11 |
| 33 | | | | | | | | | ■ | x | | | | | | | | | |
| 34 | | | | | | | | | ■ | | | | | | | | | | |
| 35 | | | | | | | | | | | | | | | | | | | |
| 43 | | | | | | | | | | | | | | | | | | | |
| 44 | | | | | | x | | | | | | | | | | | | | Hex 6 |
| 45 | | | | | | | | | | | | | | | | | | | |
| 46 | | | | | | | | | | | | | | | | | | | |
| 47 | | | | | | | | | | | | | | | | | | | |
| 48 | | | | | | | | | | | | | | | | | | | |
| 49 | | | | | | | | | x | | | | | | x | | | | Hex 15 |
| 50 | | | | | | | | | | x | | | | | x | | | | Hex 9 |
| 51 | | | | | | | | | | | | | | | | | | | |
| 52 | | . | | | | | | | | | | | | | | | | | |
| 53 | | | | | | | | | | | | | | | | | | | |
| 54 | | x | | | | | | | | | | | | | | | | | Hex 2 |
| 55 | | | | | | | | | | | | | | | | | | | |
| 56 | | | | | | | | | | | | | | | | | | | |
| 57 | | | | | | | | | | | | | | | | | | | |
| 58 | | | | | | | | | | | | | | | | | | | |
| 59 | | | | | | | | | | | | | | | | | | | |
| 60 | | | | | | | | | | | | | | | | | | | |
| 61 | | | | | | | | | | | | | | | | | | | |
| 62 | | | | | | | | | | | | | | | | | | | |
| 72 | | | | | | | | | | | | | | | | | | | |
| 73 | | | | | | | | | | | | | | | | | | | |
| 74 | | | | | | | x | | | | | | | | | | | | |
| 75 | | | | | | | | | | | | | | | | | | | Hex 7 |
| 76 | | | | | | | | | | | | | | | | | | | |
| 77 | | | | | | | | | | | | | | | | | | | |
| 78 | | | | | | | | | | | | | | | | | | | |
| 84 | | | | | | | | | | | | | | | | | | | |

FIG. 35A

| Higher Diamondoid | Compound Reference Number | M+ (m/z) (Equals Base Peak) | GC/MS Retention Times* (min.) | GC/MS Relative Retention Times** (min.) |
|---|---|---|---|---|
| Tetramantane #1 | 4-1 | 292 | 8.10 | 1.00 |
| Tetramantane #2 | 4-2 | 292 | 8.66 | 1.07 |
| Tetramantane #3 | 4-3 | 292 | 9.12 | 1.13 |
| Pentamantane #1 | 5-1 | 344 | 10.40 | 1.28 |
| Pentamantane #2 | 5-2 | 344 | 11.93 | 1.47 |
| Pentamantane #3 | 5-3 | 344 | 11.98 | 1.48 |
| Pentamantane #4 | 5-4 | 344 | 12.38 | 1.53 |
| Pentamantane #5 | 5-5 | 344 | 12.50 | 1.54 |
| Pentamantane #6 | 5-6 | 344 | 12.71 | 1.57 |
| Cyclohexamantane | C-6 | 342 | 12.34 | 1.52 |
| Hexamantane #1 | 6-1 | 396 | 14.46 | 1.78 |
| Hexamantane #2 | 6-2 | 396 | 14.61 | 1.80 |
| Hexamantane #3 | 6-3 | 396 | 14.97 | 1.85 |
| Hexamantane #4 | 6-4 | 396 | 14.99 | 1.85 |
| Hexamantane #5 | 6-5 | 396 | 15.04 | 1.86 |
| Hexamantane #6 | 6-6 | 396 | 15.13 | 1.87 |
| Hexamantane #7 | 6-7 | 396 | 15.22 | 1.88 |
| Hexamantane #8 | 6-8 | 396 | 15.32 | 1.89 |
| Hexamantane #9 | 6-9 | 396 | 15.42 | 1.90 |
| Hexamantane #10 | 6-10 | 396 | 15.45 | 1.91 |
| Hexamantane #11 | 6-11 | 396 | 15.49 | 1.91 |
| Hexamantane #12 | 6-12 | 396 | 15.54 | 1.92 |
| Hexamantane #13 | 6-13 | 396 | 15.60 | 1.93 |
| Hexamantane #14 | 6-14 | 396 | 15.81 | 1.95 |
| Hexamantane #15 | 6-15 | 396 | 15.89 | 1.96 |
| Hexamantane #16 | 6-16 | 396 | 16.05 | 1.98 |
| Hexamantane #17 | 6-17 | 396 | 16.08 | 1.99 |
| Heptamantane #1 | 7-1 | 394 | 14.96 | 1.85 |
| Heptamantane #2 | 7-2 | 394 | 15.53 | 1.92 |
| Heptamantane #3 | 7-3 | 448 | 17.34 | 2.14 |
| Heptamantane #4A | 7-4A | 448 | 17.70 | 2.18 |
| Heptamantane #4B | 7-4B | 448 | 17.70 | 2.18 |
| Heptamantane #5 | 7-5 | 448 | 17.71 | 2.19 |
| Heptamantane #6 | 7-6 | 448 | 17.79 | 2.20 |
| Heptamantane #7 | 7-7 | 448 | 17.82 | 2.20 |
| Heptamantane #8 | 7-8 | 448 | 17.99 | 2.22 |
| Heptamantane #9A | 7-9A | 448 | 18.13 | 2.24 |
| Heptamantane #9B | 7-9B | 448 | 18.13 | 2.24 |
| Heptamantane #9C | 7-9C | 448 | 18.13 | 2.24 |
| Heptamantane #10 | 7-10 | 448 | 18.15 | 2.24 |
| Heptamantane #11 | 7-11 | 448 | 18.20 | 2.25 |
| Heptamantane #12 | 7-12 | 448 | 18.21 | 2.25 |
| Heptamantane #13A | 7-13A | 448 | 18.29 | 2.26 |
| Heptamantane #13B | 7-13B | 448 | 18.29 | 2.26 |
| Heptamantane #13C | 7-13C | 448 | 18.29 | 2.26 |
| Heptamantane #14 | 7-14 | 448 | 18.32 | 2.26 |

FIG. 35A cont'd

| Higher Diamondoid | Compound Reference Number | M+ (m/z) (Equals Base Peak) | GC/MS Retention Times* (min.) | GC/MS Relative Retention Times** (min.) |
|---|---|---|---|---|
| Octamantane #1 | 8-1 | 446 | 17.30 | 2.14 |
| Octamantane #2 | 8-2 | 446 | 17.37 | 2.14 |
| Octamantane #3 | 8-3 | 446 | 17.42 | 2.15 |
| Octamantane #4 | 8-4 | 446 | 17.47 | 2.16 |
| Octamantane #5 | 8-5 | 446 | 17.71 | 2.19 |
| Octamantane #6 | 8-6 | 446 | 17.82 | 2.20 |
| Octamantane #7 | 8-7 | 446 | 17.86 | 2.20 |
| Octamantane #8 | 8-8 | 446 | 18.22 | 2.25 |
| Octamantane #9 | 8-9 | 446 | 18.46 | 2.28 |
| Octamantane #10 | 8-10 | 446 | 18.65 | 2.30 |
| Octamantane #11 | 8-11 | 446 | 18.76 | 2.32 |
| Nonamantane #1 | 9-1 | 498 | 19.86 | 2.45 |
| Decamantane #1 | 10-1 | 456 | 18.57 | 2.29 |
| Decamantane #2 | 10-2 | 496 | 21.33 | 2.63 |
| Undecamantane#1 | 11-1 | 508 | 21.05 | 2.60 |

* HP-MS5 (30m X 0.25 mm, 0.25 micron film), helium carrier gas.
** Reference to Tetramantane #1

FIG. 35B

| Higher Diamondoid | Compound Reference Number | Fraction Number | Elution Time (min.) | Elution Volume (mL) | Elution Volume Relative to 4-1 |
|---|---|---|---|---|---|
| Tetramantane #1 | 4-1 | 4 | 119 | 594 | 1.00 |
| Tetramantane #2 | 4-2 | 7 | 125 | 627 | 1.05 |
| Tetramantane #3 | 4-3 | 6 | 123 | 616 | 1.04 |
| Pentamantane #1 | 5-1 | 11 | 134 | 669 | 1.13 |
| Pentamantane #2 | 5-2 | 19 | 151 | 754 | 1.27 |
| Pentamantane #3 | 5-3 | 28 | 170 | 850 | 1.43 |
| Pentamantane #4 | 5-4 | 22 | 157 | 786 | 1.32 |
| Pentamantane #5 | 5-5 | 19 | 151 | 754 | 1.27 |
| Pentamantane #6 | 5-6 | 20 | 153 | 765 | 1.29 |
| Cyclohexamantane | C-6 | 23 | 159 | 797 | 1.34 |
| Hexamantane #1 | 6-1 | 33 | 181 | 903 | 1.52 |
| Hexamantane #2 | 6-2 | 29 | 172 | 861 | 1.45 |
| Hexamantane #3 | 6-3 | 43 | 202 | 1012 | 1.70 |
| Hexamantane #4 | 6-4 | 33 | 181 | 903 | 1.52 |
| Hexamantane #5 | 6-5 | 35 | 185 | 924 | 1.56 |
| Hexamantane #6 | 6-6 | 63 | 242 | 1211 | 2.04 |
| Hexamantane #7 | 6-7 | 37 | 189 | 945 | 1.59 |
| Hexamantane #8 | 6-8 | 39 | 193 | 967 | 1.63 |
| Hexamantane #9 | 6-9 | 39 | 193 | 967 | 1.63 |
| Hexamantane #10 | 6-10 | 48 | 214 | 1071 | 1.80 |
| Hexamantane #11 | 6-11 | 36 | 187 | 935 | 1.57 |
| Hexamantane #12 | 6-12 | 44 | 205 | 1024 | 1.72 |
| Hexamantane #13 | 6-13 | 36 | 187 | 935 | 1.57 |
| Hexamantane #14 | 6-14 | 39 | 193 | 967 | 1.63 |
| Hexamantane #15 | 6-15 | 45 | 207 | 1036 | 1.74 |
| Hexamantane #16 | 6-16 | 44 | 205 | 1024 | 1.72 |
| Hexamantane #17 | 6-17 | 49 | 217 | 1083 | 1.82 |
| Heptamantane #1 | 7-1 | 45 | 207 | 1036 | 1.74 |
| Heptamantane #2 | 7-2 | 41 | 198 | 989 | 1.66 |
| Heptamantane #3 | 7-3 | 61 | 238 | 1190 | 2.00 |
| Heptamantane #4A | 7-4A | 90 | 304 | 1519 | 2.56 |
| Heptamantane #4B | 7-4B | 90 | 304 | 1519 | 2.56 |
| Heptamantane #5 | 7-5 | 76 | 270 | 1349 | 2.27 |
| Heptamantane #6 | 7-6 | 67 | 251 | 1253 | 2.11 |
| Heptamantane #7 | 7-7 | — | — | — | — |
| Heptamantane #8 | 7-8 | 59 | 234 | 1172 | 1.97 |
| Heptamantane #9A | 7-9A | 60 | 236 | 1181 | 1.99 |
| Heptamantane #9B | 7-9B | 62 | 240 | 1200 | 2.02 |
| Heptamantane #9C | 7-9C | 78 | 274 | 1370 | 2.31 |
| Heptamantane #10 | 7-10 | 86 | 291 | 1455 | 2.45 |
| Heptamantane #11 | 7-11 | — | — | — | — |
| Heptamantane #12 | 7-12 | — | — | — | — |
| Heptamantane #13A | 7-13A | 58 | 233 | 1163 | 1.96 |
| Heptamantane #13B | 7-13B | 74 | 266 | 1328 | 2.24 |
| Heptamantane #13C | 7-13C | 90 | 304 | 1519 | 2.56 |
| Heptamantane #14 | 7-14 | 70 | 257 | 1285 | 2.16 |

FIG. 35B cont'd

| Higher Diamondoid | Compound Reference Number | Fraction Number | Elution Time (min.) | Elution Volume (mL) | Elution Volume Relative to 4-1 |
|---|---|---|---|---|---|
| Octamantane #1 | 8-1 | 81 | 280 | 1402 | 2.36 |
| Octamantane #2 | 8-2 | 83 | 285 | 1423 | 2.40 |
| Octamantane #3 | 8-3 | 64 | 244 | 1221 | 2.06 |
| Octamantane #4 | 8-4 | — | — | — | — |
| Octamantane #5 | 8-5 | 63 | 242 | 1211 | 2.04 |
| Octamantane #6 | 8-6 | 79 | 276 | 1381 | 2.32 |
| Octamantane #7 | 8-7 | 71 | 259 | 1296 | 2.18 |
| Octamantane #8 | 8-8 | 84 | 287 | 1434 | 2.41 |
| Octamantane #9 | 8-9 | 74 | 266 | 1328 | 2.24 |
| Octamantane #10 | 8-10 | 80 | 280 | 1402 | 2.36 |
| Octamantane #11 | 8-11 | 85 | 289 | 1445 | 2.43 |
| Nonamantane #1 | 9-1 | 89 | 297 | 1487 | 2.50 |
| Decamantane #1 | 10-1 | 83 | 285 | 1423 | 2.40 |
| Decamantane #2 | 10-2 | — | — | — | — |
| Undecamantane#1 | 11-1 | 101 | 355 | 1774 | 2.99 |

ODS HPLC Whatman ODS-II 10/50
(2 Columns in series), acetone mobile phase @5.0 mL/min.

FIG. 37
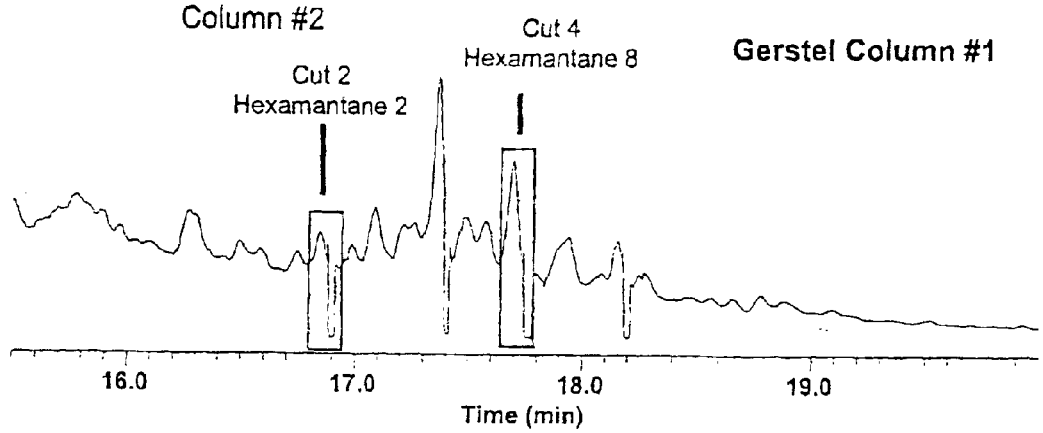
A) Peaks Cut and Sent to Column #2 — Gerstel Column #1
Cut 2 Hexamantane 2
Cut 4 Hexamantane 8
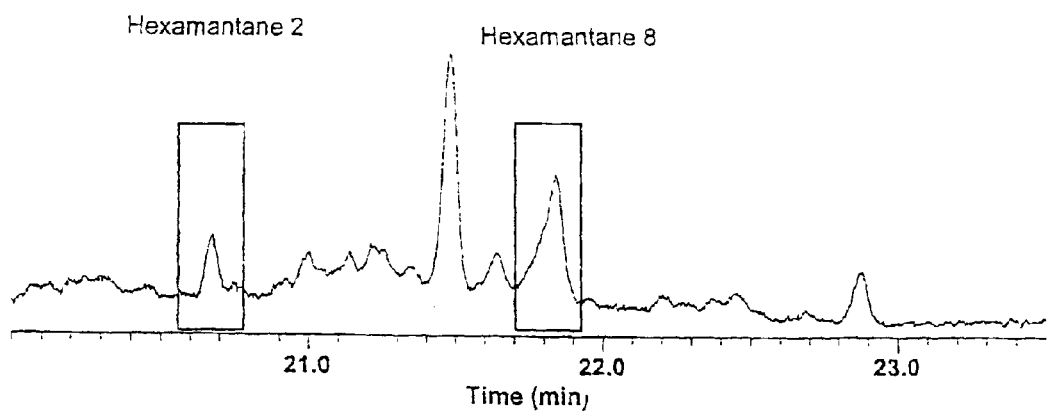
B) Peaks Sent to Traps
Where Crystals of Hexamantane #2 (trap 1) and #8 (trap 3) formed — Gerstel Column #2
Hexamantane 2
Hexamantane 8

FIG. 38
A)
Crystal of Nonamantane (Mol. Wt. 498)
B)
Mass Spectrum of Dissolved Crystal of Nonamantane
Retention time 19.83 min.
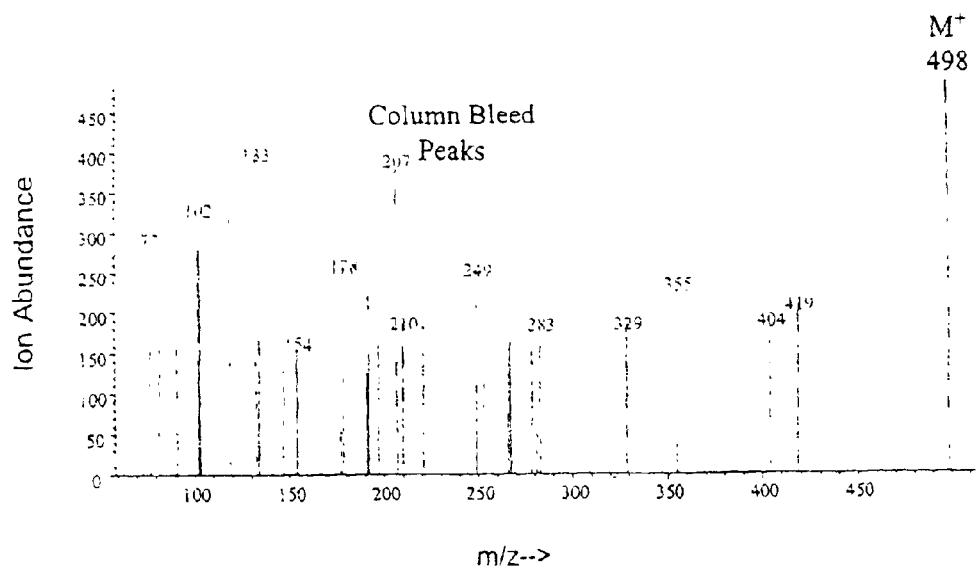

FIG. 39
Total Ion Chromatogram
A)
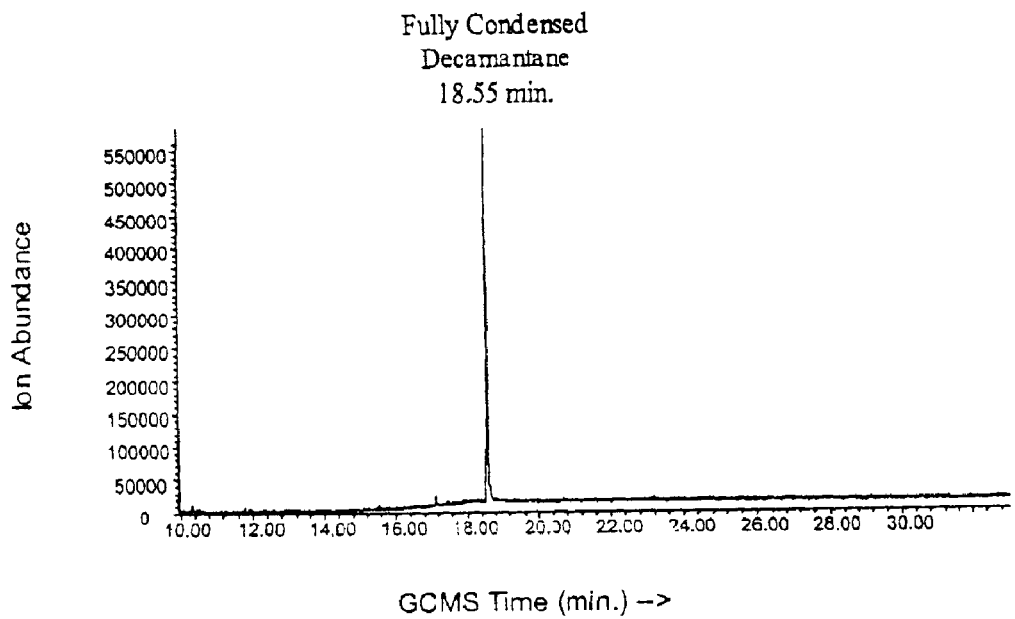
GCMS Time (min.) -->
B)
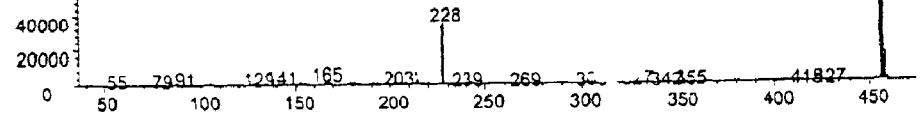
m/z-->

FIG. 40
A) Crystal of Fully Condensed Decamantane
B) Mass Spectrum of Dissolved Crystal of Fully Comndensed Decamantane
Retention time 18.54 min.
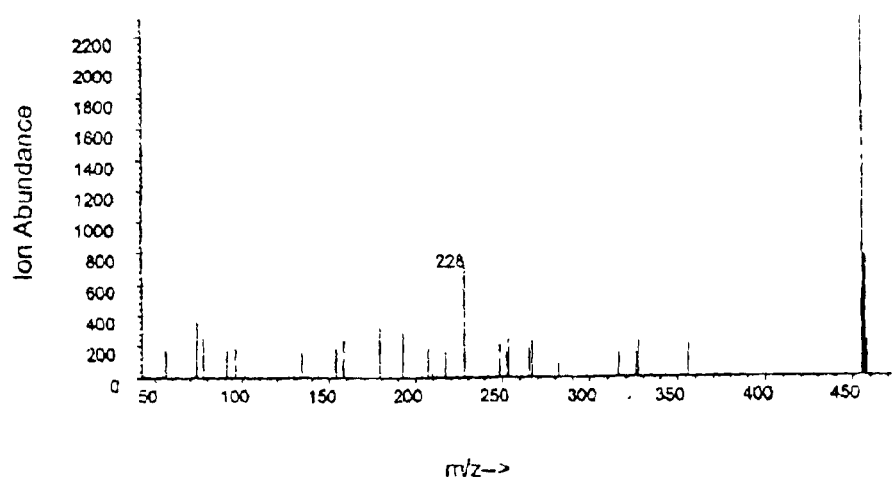

PROCESSES FOR THE PURIFICATION OF HIGHER DIAMONDOIDS AND COMPOSITIONS COMPRISING SUCH DIAMONDOIDS

This application is a continuation-in-part of U.S. patent application Ser. No. 10/017,821, filed Dec. 12, 2001, incorporated herein by reference. This application also claims the benefit under 35 U.S.C. §119 to U.S. Provisional Application Ser. No. 60/262,842, filed Jan. 19, 2001 which application is incorporated herein by reference in its entirety.

BACKGROUND OF THE INVENTION

This invention is directed to novel processes for the recovery and at least partial purification of higher diamondoid components from hydrocarbonaceous feedstocks. Specifically, this invention is directed to recovery processes for obtaining compositions enhanced in one or more higher diamondoid components.

This invention is also directed to compositions comprising enriched levels of one or more higher diamondoids.

The following publications and patents are cited in this application as superscript numbers:

[1] Fort, Jr., et al., *Adamantane: Consequences of the Diamondoid Structure*, Chem. Rev 64., :277–300 (1964)

[2] Sandia National Laboratories (2000), *World's First Diamond Micromachines Created at Sandia*, Press Release, (Feb. 22, 2000) www.Sandia.gov.

[3] Lin, et al., *Natural Occurrence of Tetramantane ($C_{22}H_{28}$), Pentamantane ($C_{26}H_{32}$) and Hexamantane ($C_{30}H_{36}$) in a Deep Petroleum Reservoir*, Fuel 74, (10) :1512–1521 (1995)

[4] Chen, et al., Isolation of High Purity Diamondoid Fractions and Components, U.S. Pat. No. 5,414,189, issued May 9, 1995

[5] Alexander, et al., Removal of Diamondoid Compounds from Hydrocarbonaceous Fractions, U.S. Pat. No. 4,952,747, issued Aug. 28, 1990

[6] Alexander, et al., Purification of Hydrocarbonaceous Fractions, U.S. Pat. No. 4,952,748, issued Aug. 28, 1990

[7] Alexander, et al., Removal of Diamondoid Compounds from Hydrocarbonaceous Fractions, U.S. Pat. No. 4,952,749, issued Aug. 28, 1990

[8] Alexander, et al., Purification of Hydrocarbonaceous Fractions, U.S. Pat. No. 4,982,049, issued Jan. 1, 1991

[9] Swanson, Method for Diamondoid Extraction Using a Solvent System, U.S. Pat. No. 5,461,184, issued Oct. 24, 1995

[10] Partridge, et al., Shape-Selective Process for Concentrating Diamondoid-Containing Hydrocarbon Solvents, U.S. Pat. No. 5,019,665, issued May 28, 1991

[11] Dahl, et al., Diamondoid *Hydrocarbons as Indicators of Natural Oil Cracking*, Nature, 54–57 (1999).

[12] McKervey, Synthetic *Approaches to Large Diamondoid Hydrocarbons, Tetrahedron* 36, :971–992 (1980).

[13] Wu, et al., High Viscosity Index Lubricant Fluid, U.S. Pat. No. 5,306,851, issued Apr. 26, 1994.

[14] Chung et al., Recent *Development in High-Energy Density Liquid Fuels*, Energy and Fuels 13, 641–649 (1999).

15 Balaban et al., *Systematic Classification and Nomenclature of Diamond Hydrocarbons-I*, Tetrahedron 34, 3599–3606 (1978).

All of the above publications and patents are herein incorporated by reference in their entirety to the same extent as if each individual publication or patent was specifically and individually indicated to be incorporated by reference in its entirety.

Diamondoids are cage-shaped hydrocarbon molecules possessing amazingly rigid structures that are superimposable fragments of the diamond crystal lattice[1] (see FIG. 1). Adamantane, a ten-carbon molecule, is the smallest member of the diamondoid series, consisting of one diamond crystal subunit. Diamantane contains two face-fused diamond subunits, triamantane three, tetramantane four, and so on. While there is only one isomeric form of adamantane, diamantane and triamantane, there are four different isomeric tetramantanes; four different shapes containing four diamond subunits that can be superimposed on the diamond crystal lattice. Two of these isomers are enantiomeric (mirror images of each other). The number of possible isomers increases rapidly with each higher member of the diamondoid series. Because diamondoid crystal units can share more than a single face in some higher diamondoids, hydrogen to carbon ratios, i.e., the degree of condensation, also show increasing variation resulting in an increasing variety of molecular weights for each successive higher diamondoid family. FIG. 30 is a table depicting the range of higher diamondoids.

The parent diamondoids may be substituted with alkyls at various sites, and a myriad of methyl, ethyl, dimethyl, trimethyl, propyl, etc., substituted species are possible and occur naturally in petroleum feedstocks along with the parent diamondoids. Diamondoids are present in virtually every petroleum (oils and gas condensates) as well as oil source-rock extracts.[11] The natural concentration of diamondoids in petroleum varies by orders of magnitude. For instance, methyldiamantane concentrations in relatively low-maturity crude oils from the central valley of California, are on the order of a few parts per million (ppm). Low-maturity oils sourced from the Jurassic-age Smackover Formation, Gulf Coast, USA, have methyldiamantane concentrations of 20–30 ppm. Deeply-buried petroleums such as gas condensate from deep formation, which have undergone substantial cracking as a result of intense heat, may have methyldiamantane concentration in the thousands of ppms.

The high diamondoid concentrations of some gas condensates and other feedstocks occur because of the high thermal stability of diamondoids compared to the other petroleum components. These diamondoids may be remnants of petroleum degradation by a geologic process over time and temperature conditions where other hydrocarbons were thermally cracked or reduced to gas and pyrobitumen. Because of this natural concentrating mechanism, in some gas condensates, diamondoids may become the dominant species. In addition, because they are extremely stable molecules, diamondoids survive and become concentrated in certain refinery streams after processing, e.g., cracking, hydrocracking, etc. The art has come to refer to adamantane, diamantane, triamantane and substituted analogs thereof as "lower diamondoids". Tetramantane and larger diamondoids and substituted analogs are referred as "higher diamondoids". That nomenclature is used herein. The lower diamondoid components show no isomers or chirality and are readily synthesized, distinguishing them from "higher diamondoids".

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum trioxide ($Al_2O_3$) and excellent thermal conductivity.

In addition, tetramantane and other higher diamondoids have sizes in the nanometer range and, in view of the properties noted above, the inventors contemplate that such compounds would have utility in micro- and molecular-electronics and nanotechnology applications. In particular, the rigidity, strength, stability, thermal conductivity, variety of structural forms and multiple attachment sites shown by these higher diamondoid molecules makes possible accurate construction of robust, durable, precision devices with nanometer dimensions. It has been estimated that Micro-ElectroMechanical Systems (MEMs) constructed out of diamond should last 10,000 times longer then current polysilicon MEMs, and diamond is chemically benign and would not promote allergic reactions in biomedical applications.[2] The higher diamondoids would have similar attractive properties. Furthermore, some of the many isomers of the higher diamondoids possess chirality, offering opportunities for making nanotechnology objects of great structural specificity and ones which have useful optical properties. Applications of these higher diamondoids include molecular electronics, photonics, nanomechanical devices, and nano-structured polymers and other materials.

Notwithstanding the advantages of tetramantane and other higher diamondoids, the art fails to readily provide for compositions comprising these higher diamondoids.

For example, while Lin, et al.[3] report the natural occurrence of tetramantane, pentamantane and hexamantane in deep petroleum reservoirs. However, they were only able to tentatively identify such compounds in ionized form as part of a mass spectroscopy analysis.

Likewise, while Chen, et al.[4] discloses methods for isolation of high purity lower diamondoid fractions and components, the disclosed methods provide for distilling a diamondoid-comprising feedstock into 5 overhead components. These overhead components include unsubstituted adamantane, substituted adamantane, unsubstituted diamantane, substituted diamantane, and unsubstituted triamantane. Chen, et al. further recite that the pot material recovered after said distillation comprises a major amount of substituted triamantane and minor amounts of tetramantane and pentamantane. There was, however, no disclosure in Chen, et al. of the relative amounts of tentatively identified tetramantane and pentamantane in the pot material and Table 3 of Chen indicates only the presence of triamantane and tetramantane in the pot material and no attempt to isolate any high diamondoid is reported.

Other efforts to recover diamondoid fractions from naturally-occurring hydrocarbonaceous feedstocks have dealt with recovering the lower diamondoids illustrated by adamantane, diamantane and triamantane and various side-chain-containing analogues thereof primarily for the purpose of recovering these components from a natural gas stream in order to prevent operational problems in natural gas productions due to precipitation of these components in the production equipment. See, for example, the four related patents to Alexander, et al.[5-8] One or more of these patents disclose: 1) extracting lower diamondoids from a gas stream with a solvent and further extraction by sorption on silica gel; 2) extracting lower diamondoids by use of a heat exchanger; 3) extracting lower diamondoids from a gas stream using a porous solid such as zeolite. Recovery of lower diamondoids from a gas stream is also disclosed by Swanson[9] and recovery of lower diamondoids from a liquid stream is disclosed by Partridge, et al.[10]

While synthetic routes to prepare diamondoids have provided for all of the lower diamondoids (adamantane through triamantane) by carbocation-mediated, thermo-dynamically controlled super-acid equilibration, this synthetic route, when applied to the synthesis of tetramantane and other higher diamondoids is blocked by severe kinetic (mechanistic) constraints. All attempts to synthesize the higher diamondoids by this thermodynamic equilibration route have proven futile. McKervey, et al.[12] have reported, however, the synthesis in low yields (e.g., ~10%) of anti-tetramantane from 1,6-dicarboxyl diamanatane using in the final step of the synthesis a gas-phase rearrangement over a platinum catalyst at 360° C. As is apparent, the use of such a starting material coupled with its low availability renders this synthetic procedure commercially unattractive and, moreover, it does not provide for the synthesis of other tetramantanes or other higher diamondoids.

In view of the above, there is an ongoing need in the art to provide for compositions comprising tetramantane and other higher diamondoids thereof. In view of the synthetic difficulties, there is also a need in the art to develop processes for recovering tetramantane and other higher diamondoids from natural sources.

SUMMARY OF THE INVENTION

This invention is directed to novel processes for providing compositions enriched in higher diamondoids from a hydrocarbonaceous feedstock comprising recoverable amounts of these higher diamondoid components.

In a first aspect, the processes of this invention entail removing at least a portion of the components from the feedstock having a boiling point lower than the lowest boiling point higher diamondoid component selected for recovery and subsequently pyrolytically treating the feedstock under conditions wherein recoverable amounts of the selected higher diamondoid component or components are retained in the pyrolytically-treated feedstock. Accordingly, in this first aspect, this invention is directed to a process which comprises:

a) selecting a feedstock comprising recoverable amounts of a higher diamondoid component or components selected for recovery;

b) removing a sufficient amount of components from the feedstock having a boiling point less than the lowest boiling point higher diamondoid component selected for recovery under conditions wherein recoverable amounts of the higher diamondoid component or components selected for recovery are retained in the treated feedstock which is recovered; and c) thermally treating the treated feedstock recovered in b) above to pyrolyze at least a sufficient amount of non-diamondoid components therefrom to permit recovery of the selected higher diamondoid component or components from the pyrolytically-treated feedstock wherein the pyrolysis is conducted under conditions to provide for a thermally treated feedstock retaining recoverable amounts of the selected higher diamondoid component or components.

In common hydrocarbonaceous feedstocks, components having a boiling point less than the lowest boiling selected higher diamondoid component typically include nondiamondoid components as well as lower diamondoid components. Accordingly, in another of its process aspects, this invention is directed to a process for recovering a composition enriched in one or more selected higher diamondoid components which process comprises:

a) selecting a feedstock comprising recoverable amounts of a selected higher diamondoid component or components, nondiamondoid components having a boiling point both below and above the lowest boiling point selected higher diamondoid component, and at least one lower diamondoid component;

b) removing a sufficient amount of nondiamondoid components having a boiling point below the lowest boiling point selected higher diamondoid component as well as lower diamondoid components from the feedstock under conditions to provide a treated feedstock wherein the selected higher diamondoid component or components are retained therein; and c) thermally treating said treated feedstock recovered in b) to pyrolyze at least a sufficient amount of nondiamondoid components therefrom to permit recovery of the selected higher diamondoid components from the pyrolytically-treated feedstock.

The order of the procedures for removal of the lower boiling point components and the pyrolysis of the feedstock are interchangeable. Accordingly, a further aspect of this invention is directed to a process for recovering a composition enriched in a selected higher diamondoid component or components which process comprises:

a) selecting a feedstock comprising recoverable amounts of a selected higher diamondoid component or components;

b) thermally treating the feedstock to pyrolyze at least a sufficient amount of nondiamondoid components therefrom to permit recovery of the selected higher diamondoid component or components from the pyrolytically-treated feedstock wherein said pyrolysis is conducted under conditions to provide for a treated feedstock retaining recoverable amounts of the selected higher diamondoid component or components; and c) removing a sufficient amount of those components from the feedstock surviving pyrolysis which components have a boiling point less than the lowest boiling point selected higher diamondoid component under conditions wherein recoverable amounts of the selected higher diamondoid component or components are retained in the treated feedstock.

It is understood, however, that due to their thermal stability, the components surviving pyrolysis which have a boiling point less than the lowest boiling selected higher diamondoid component will include at least a portion of the lower diamondoids originally present in the feedstock. Accordingly, still a further aspect of this invention is directed to a process for recovering a composition enriched in a selected higher diamondoid component or components which process comprises:

a) selecting a feedstock comprising recoverable amounts of a selected higher diamondoid component or components, nondiamondoid components, and at least one lower diamondoid component;

b) thermally treating said feedstock to pyrolyze at least a portion of the nondiamondoid components under conditions wherein recoverable amounts of the selected higher diamondoid component or components are retained in said pyrolytically treated feedstock; and c) removing a sufficient amount of lower diamondoid components from the pyrolytically treated feedstock under conditions to provide a treated feedstock from which the selected higher diamondoid component or components can be recovered.

It will be appreciated that in all of these aspects of the invention, it is possible, and often likely, that the higher diamondoid-containing feedstocks will contain several higher diamondoid components some of which are to be selected and some of which are not to be selected. Depending upon which of these higher diamondoid components are present and which of these are selected, it is possible that there will be nonselected higher diamondoids having a boiling point below the lowest boiling point of the lowest boiling point selected higher diamondoids. These lower boiling nonselected higher diamondoids may be removed, at least partially, with the other lower boiling components, such as the lower diamondoids.

When employing feedstocks sufficiently free of nondiamondoid materials, recovery of tetramantane components and pentamantane components do not always require thermal pyrolysis to effect their recovery. When thermal pyrolysis is not employed, after removal of the lower diamondoid components, the tetramantane components and pentamantane components can be recovered from the treated feedstock by separation techniques disclosed herein. Accordingly, in another of its process aspects, this invention is directed to a process for recovering a composition enriched in tetramantane and pentamantane components which process comprises:

a) selecting a feedstock comprising recoverable amounts of tetramantane and pentamantane components and at least one lower diamondoid component and;

b) removing a sufficient amount of the lower diamondoid components from the feedstock under conditions to provide a treated feedstock from which tetramantane and pentamantane components can be recovered; and c) recovering tetramantane and pentamantane components from said treated feedstock by separation techniques selected from the group consisting of chromatographic techniques, thermal diffusion techniques, zone refining, progressive recrystalization and size separation techniques.

In a preferred embodiment for each of the above processes, the feedstock employed therein comprises at least about 1 ppb (more preferably at least about 25 ppb and still more preferably at least about 100 ppb of selected higher diamondoid components.

In another preferred embodiment for each of the above processes, sufficient amounts of lower diamondoid components are removed from the feedstock to provide a ratio of lower diamondoid components (triamantane components and lower) to higher diamondoid components (tetramantane components and higher) of no greater than 9:1; more preferably, a ratio of no greater than 2:1; and even more preferably, a ratio of no greater than 1:1.

In still another preferred embodiment for each of the above processes, after removal of the lower diamondoid components from the feedstock, at least about 10%, more preferably at least 50% and still more preferably at least 90% of said higher diamondoids components are retained in the feedstock as compared to that amount found in the feedstock prior to the removal.

In yet another preferred embodiment, after pyrolysis of the feedstock, at least about 10%, more preferably at least about 50%, and still more preferably at least about 90% of said higher diamondoid components are retained in the feedstock after pyrolytic treatment compared to that amount found in the feedstock prior to pyrolytic treatment.

Preferably, the recovered feedstock produced by the above processes is further purified by chromatography, membrane size separation, crystallization, sublimation and the like.

In one of its product aspects, this invention provides for a composition comprising at least tetramantane and pentamantane components wherein said composition comprises at least about 10 weight percent tetramantane components and at least about 0.5 weight percent pentamantane components based on the total weight of the diamondoids in the composition.

In yet another preferred embodiment, this invention provides for a composition comprising at least tetramantane and pentamantane components wherein said composition comprises at least about 25 weight percent tetramantane components, still more preferably at least about 50 weight percent tetramantane components, and at least about 0.5 weight percent pentamantane components based on the total weight of the diamondoids in the composition.

Preferably, this composition further comprises hexamantane and higher components. More preferably, the hexamantane components found in any such composition do not include the fully condensed cyclohexamantane of the formula $C_{26}H_{30}$ and having a molecular weight of 342.

In still another of its product aspects, this invention provides for a preferred composition comprising at least tetramantane and pentamantane components wherein said composition comprises at least about 10 weight percent tetramantane components and at least about 0.5 weight percent pentamantane components based on the total weight of the composition. More preferably, such compositions comprise at least about 25 weight percent tetramantane components, and still more preferably at least about 50 weight percent tetramantane components, and at least about 0.5 weight percent pentamantane components based on the total weight of the composition.

Preferably, this composition further comprises hexamantane and other higher diamondoid components.

BRIEF DESCRIPTION OF THE DRAWINGS

In FIG. 9, the GC/MS total ion current chromatogram illustrates the presence of higher diamondoids at levels allowing isolation. In FIG. 10, the GC/MS ion chromatogram (m/z 394) illustrates the presence of a molecular weight 394 heptamantane. In FIG. 11, the GC/MS total ion chromatogram (TIC) illustrates the presence of heptamantanes at levels allowing isolation.

FIG. 19 illustrates GC/MS total ion current chromatogram of HPLC fraction #6 (FIG. 17), showing one major component and selected ion chromatogram of fraction #6 (m/z 292) demonstrating that this component is one of the tetramantane isomers.

FIG. 27A is a photomicrograph of crystals of pentamantane #1 (mol. wt. 344) isolated from Feedstock B by preparative capillary gas chromatography.

FIG. 27B is a GC/MS total ion current chromatogram and 27C is the mass spectrum showing the purity of this isolated pentamantane.

FIG. 28A is a photomicrograph of crystals of hexamantane #8 (mol. wt. 396) isolated from Feedstock B by preparative capillary gas chromatography.

FIG. 28B is a GC/MS total ion current chromatogram and 28C is the mass spectrum showing the purity of this isolated hexamantane.

FIG. 29A is a photomicrograph of crystals of a fully condensed heptamantane (mol. wt. 394) isolated from Feedstock B by preparative capillary gas chromatography.

FIG. 29B is a GC/MS total ion current chromatogram and 29C is the mass spectrum showing the purity of this isolated heptamantane.

FIG. 30 is a table depicting the number of different molecular weights in each higher diamondoid series and the value of those molecular weights.

FIG. 31 is a distillation chart illustrating distillation cuts on a higher diamondoid-containing feedstock selected to favor the enrichment of selected various higher diamondoids.

FIGS. 32 and 33 are charts illustrating elution sequences for a variety of individual higher diamondoids on two different chromatography columns: ODS and Hypercarb.

FIGS. 35A and 35B are compilations of the GC/MS and HPLC properties of various higher diamondoids included in this application.

FIGS. 37A and 37B illustrate the preparative capillary gas chromatographic data for hexamantane isolations. FIG. 37A, shows the first column cuts containing two of the hexamantanes from Feedstock B. FIG. 37B, shows the second column peaks isolated and sent to the traps. From this procedure pure hexamantanes were isolated, hexamantane #2, the second hexamantane to elute in our GC/MS assay, while hexamantane #8 is the eighth to elute.

FIG. 38A is photomicrograph of a nonamantane crystal.

FIG. 38B is a mass spectrum of a dissolved nonamantane crystal.

FIG. 39A is the GC/MS of isolated, fully condensed decamantane with a mass spectrum of this material shown in FIG. 39B.

FIG. 40A is a photomicrograph of a crystal of fully condensed decamantanes.

FIG. 40B is a mass spectrum of a dissolved decamantane crystal of FIG. 40A.

DETAILED DESCRIPTION OF THE INVENTION

Figure 1:
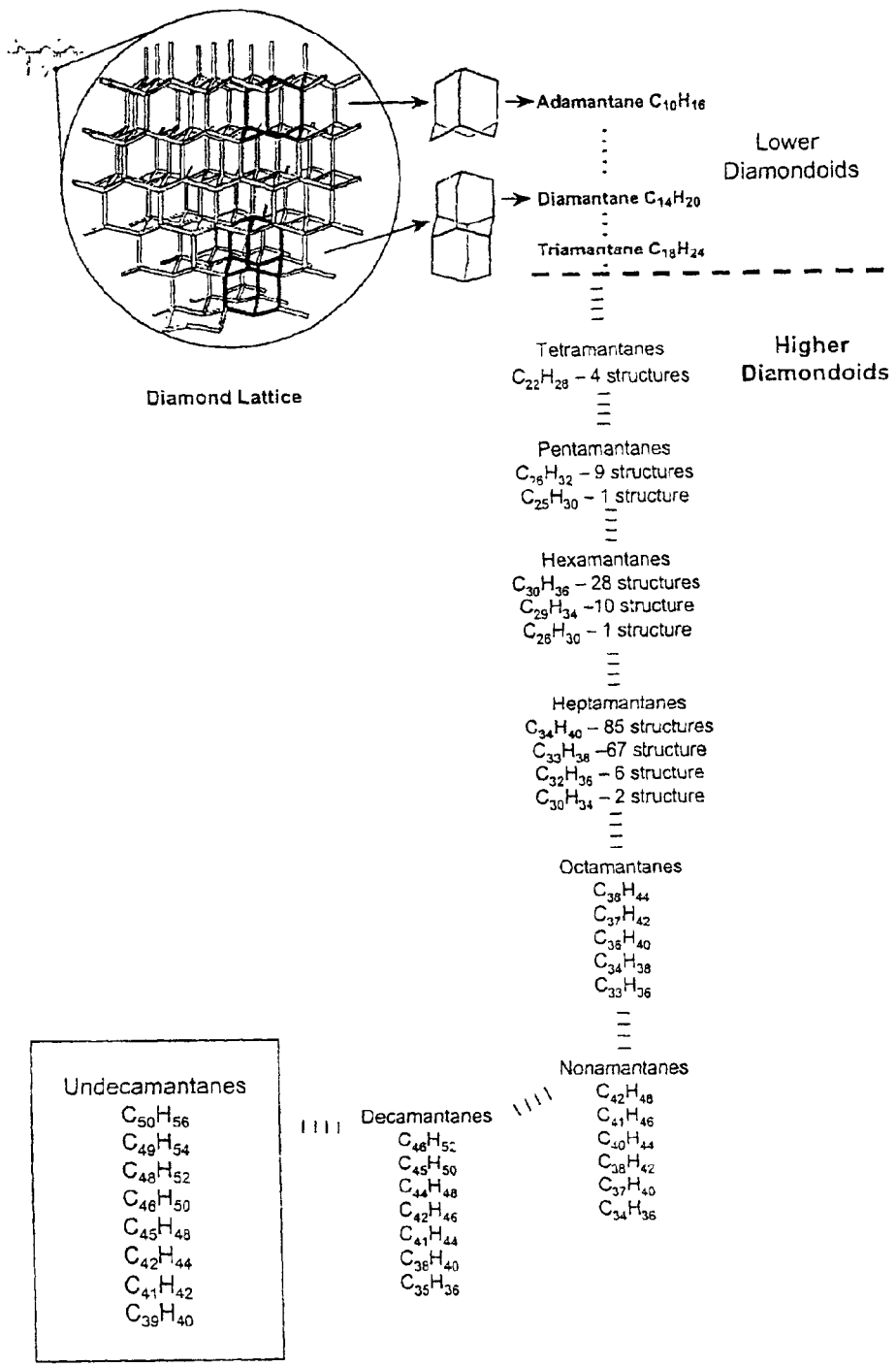
FIG. 1 illustrates the cage-shaped structure of diamondoids and their correlation to diamonds. Specifically, illustrated is the correlation of the structures of diamondoids to subunits of the diamond crystal lattice.

This invention is directed to processes for the recovery and purification of higher diamondoid components from hydrocarbonaceous feedstocks as well as compositions comprising such higher diamondoids. However, prior to describing this invention in further detail, the following terms will first be defined.

As used herein, the following terms have the following meanings.

The term "diamondoid" refers to substituted and unsubstituted caged compounds of the adamantane series including adamantane, diamantane, triamantane, tetramantane, pentamantane, hexamantane, heptamantane, octamantane, nonamantane, decamantane, undecamantane, and the like and also including all isomers and stereoisomers thereof. Substituted diamondoids preferably comprise from 1 to 10 and more preferably 1 to 4 alkyl substituents.

The term "lower diamondoid components" or "adamantane, diamantane and triamantane components" refers to any and/or all unsubstituted and substituted derivatives of adamantane, diamantane and triamantane.

The term "higher diamondoid components" refers to any and/or all substituted and unsubstituted diamondoids corresponding to tetramantanes and above including tetramantanes, pentamantanes, hexamantanes, heptamantanes, octamantanes, nonamantanes, decamantanes, undecamantanes, and the like including all isomers and stereoisomers thereof. Preferably, the higher diamondoids include substituted and unsubstituted tetramantanes, pentamantanes, hexamantanes, heptamantanes, octamantanes, nonamantanes, decamantanes and undecamantanes. FIG. 30 is a Table which shows representative higher diamondoids together with their molecular weights.

The term "tetramantane components" refer to any and/or all substituted and unsubstituted diamondoids corresponding to tetramantane.

The term "pentamantane components" refer to any and/or all substituted and unsubstituted diamondoids corresponding to pentamantane. The term "non-ionized diamondoid components" refers to higher diamondoid components which do not carry a charge such as a positive charge generated during mass spectral analysis wherein the phrase "higher diamondoid components" is as defined herein.

The term "non-ionized tetramantane components" refers to tetramantane components which do not carry a charge such as a positive charge generated during mass spectral analysis.

The term "non-ionized pentamantane components and diamondoid components higher than pentamantane" refers to pentamantane components and higher diamondoid components larger than pentamantane which do not carry a charge such as a positive charge generated during mass spectral analysis.

The terms "selected higher diamondoid components" and the like refers to that one or more substituted or unsubstituted higher diamondoids that are desired to be isolated or "enriched" in a product.

The terms "nonselected higher diamondoid components" and the like refer to those higher diamondoids that are not "selected higher diamondoids".

The term "enriched" when used to describe the state of purity of one or more higher diamondoid components refers to such materials at least partially separated from the feedstock, and in the case of "enriched" individual higher diamondoid components, concentrated at least 25 and preferably at least 100 times the original concentration exhibited in the feedstock. Preferably "enriched" higher diamondoid or "enriched" higher diamondoid components make up at least 25%, especially at least 50% (i.e., 50–100%), more preferably at least 75% and yet more preferably at least 95% or even at least 99% by weight of the overall material in which they are present or in other words exhibit a weight purity of at least 25%, 50%, 75%–95% or 99% of such material.

The term "feedstock" or "hydrocarbonaceous feedstock" refers to hydro-carbonaceous materials comprising recoverable amounts of higher diamondoids. Preferably, such feedstocks include oil, gas condensates, refinery streams, oils derived from reservoir rocks, oil shale, tar sands, and source rocks, and the like. Such components typically, but not necessarily, comprise one or more lower diamondoid components as well as nondiamondoid components. The latter is typically characterized as comprising components having a boiling point both below and above the lowest boiling point tetramantane which boils at about 350° C. at atmospheric pressure. Typical feedstocks may also contain impurities such as sediment, metals including nickel, vanadium and other inorganics. They may also contain heteromolecules containing sulfur, nitrogen and the like. All of these non-diamondoid materials are included in "nondiamondoid components" as that term as defined herein.

The term "nonselected materials" refers to the collection of feedstock components that are not "selected higher diamondoids and include "nondiamondoid components", "lower diamondoids" and "nonselected higher diamondoid" as these terms are defined herein.

The term "remove" or "removing" refers to processes for removal of nondiamondoid components and/or lower diamondoid components and/or nonselected higher diamondoid components from the feedstock. Such processes include, by way of example only, size separation techniques, distillation, evaporation either under normal or reduced pressure, well-head separators, sorption, chromatography, chemical extraction, crystallization and the like. For example, Chen, et al.[4] disclose distillation processes for removing adamantane, substituted adamantane, diamantane, substituted diamantane, and triamantane from a hydrocarbonaceous feedstock. Size separation techniques include membrane separations, molecular sieves, gel permeation, size exclusion chromatography and the like.

The terms "distillation" or "distilling" refers to atmospheric, reduced pressure distillation, and elevated pressure distillation processes on the hydrocarbonaceous feedstock which are conducted under conditions wherein the distillation is terminated when a portion and, preferably, at least 50 weight percent of adamantane, diamantane and triamantane components is removed from the feedstock. Unless otherwise specified, distillation temperatures are reported as atmospheric equivalents.

The terms "fractionation" and "fractionating" refer to processes in which materials in a mixture of materials are separated from each other such as by differential solubility, differential vapor pressure, differential chromatographic affinity and the like.

The terms "thermal treating to pyrolysis" and the like refer to either atmospheric, reduced pressure or elevated pressure heating of the feedstock or a feedstock fraction to pyrolyze a portion of one or more components in the feedstock.

The term "nondiamondoid components of a feedstock" refers to components of the feedstock or a feedstock fraction which are not diamondoid in character wherein the term "diamondoid" is as defined herein.

The term "retained" refers to retention of at least a portion of the higher diamondoid components found in the recovered feedstock when compared to the amount of such diamondoids found in the original feedstock. In a preferred embodiment, at least about 10 weight percent of the higher diamondoid components are retained in the recovered feedstock; more preferably, at least about 50 weight percent of the higher diamondoid components are retained in the recovered feedstock; and still more preferably, at least about 90 weight percent of the higher diamondoid components are retained in the recovered feedstock; each based on the total amount of such diamondoids found in the feedstock prior to treatment.

The term "chromatography" refers to any of a number of well known chromatographic techniques including, by way of example only, column or gravity chromatography (either normal or reverse phase), gas chromatography, high performance liquid chromatography, and the like.

The term "alkyl" refers to straight and branched chain saturated aliphatic groups typically having from 1 to 20 carbon atoms, more preferably 1 to 6 atoms ("lower alkyls"), as well as cyclic saturated aliphatic groups typically having from 3 to 20 carbon atoms and preferably from 3 to 6 carbon atoms ("lower alkyls" as well). The terms "alkyl" and "lower alkyl" are exemplified by groups such as methyl, ethyl, propyl, butyl, isopropyl, isobutyl, sec-butyl, t-butyl, n-heptyl, octyl, cyclopropyl, cyclobutyl, cyclopentyl, cyclohexyl and the like.

Methodology

The processes of this invention can be conducted with readily available feedstocks using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures.

Furthermore, the higher diamondoids of this invention will typically contain one or more isomers or stereoisomers and substituted diamondoids will typically contain one or more chiral centers. Accordingly, if desired, such compounds can be prepared or isolated as pure isomers or stereoisomers, e.g., as individual enantiomers or diastereomers, or as stereoisomer-enriched mixtures. All such isomers and stereoisomers (and enriched mixtures) are included within the scope of this invention, unless otherwise indicated. Pure stereoisomers (or enriched mixtures) may be prepared using, for example, crystallizations, optically active solvent or stereoselective reagents well-known in the art. Alternatively, racemic mixtures of such compounds can be separated using, for example, chiral column chromatography, chiral resolving agents and the like.

In the processes of this invention, a feedstock is selected such that said feedstock comprises recoverable amounts of one or more selected higher diamondoid components. Preferably, such feedstock comprises at least about 1 ppb of one or more higher diamondoid components, more preferably, at least about 25 ppb and still more preferably at least about 100 ppb. It is understood, of course, that feedstocks having higher concentrations of higher diamondoid components facilitate recovery of these components.

Preferred feedstocks include, for example, natural gas condensates and refinery streams having high concentrations of higher diamondoids. With regard to the latter, such refinery streams include hydrocarbonaceous streams recoverable from cracking processes, distillations, coking and the like. Particularly preferred feedstocks include gas condensates feedstocks recovered from the Norphlet Formation in the Gulf of Mexico and from the LeDuc Formation in Canada.

Figure 20:
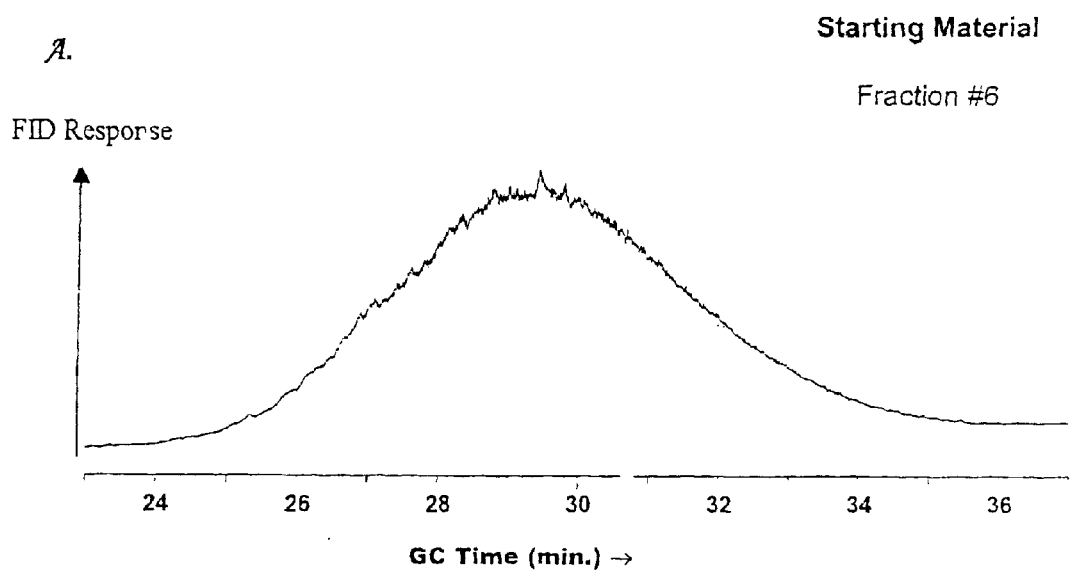
FIG. 20A illustrates a gas chromatogram (FID) of the distillate fraction #6 (Table 3B) of Feedstock B 650° F.+ distillation bottoms.
FIG. 20B shows the resulting product of pyrolytic processing this feedstock, showing the nondiamondoid components have been degraded and pentamantanes, hexamantanes and highly condensed heptamantanes components that have become available for isolation.
Figure 21:
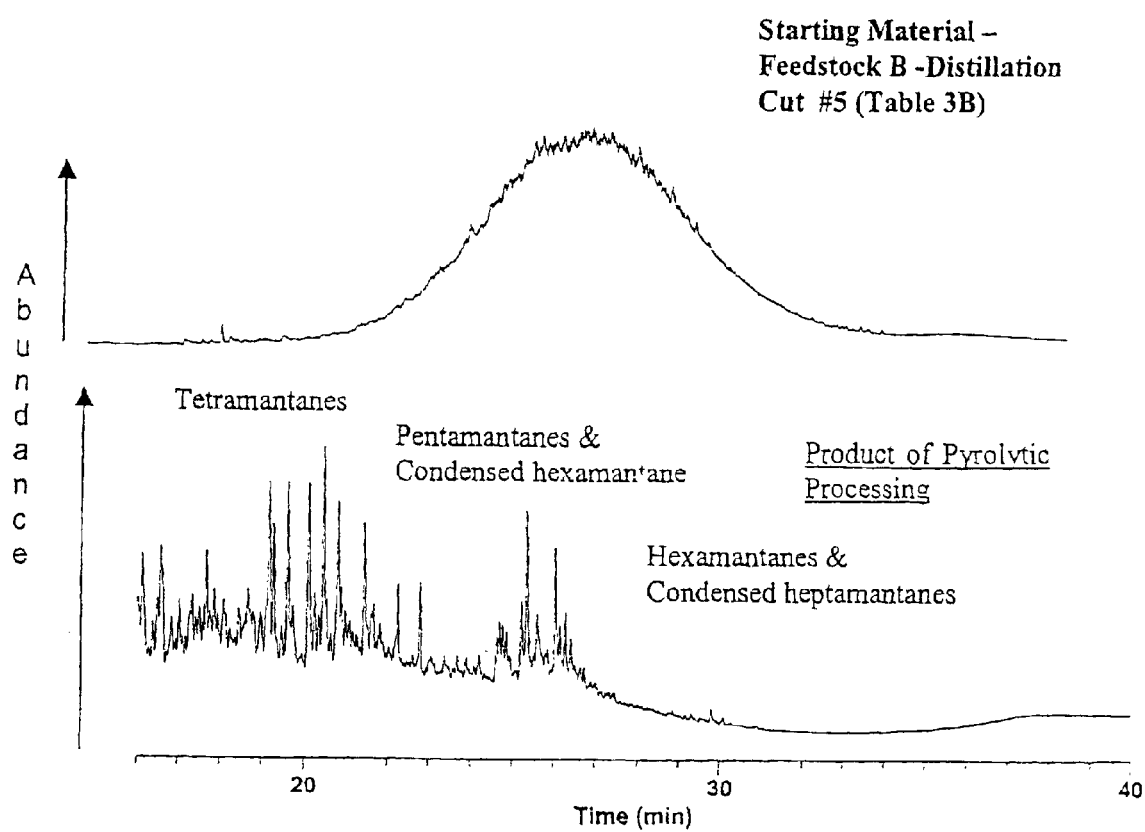
FIG. 21 illustrates a gas chromatogram (FID) of distillate fraction #5 (Table 3B) of Feedstock B 650° F.+ distillation bottoms, and the resulting product of pyrolytic processing showing nondiamondoid components have been destroyed and tetramantanes, pentamantanes, hexamantanes and highly condensed heptamantanes that have become available for isolation.

In one embodiment, the feedstocks used in the processes of this invention typically comprise nondiamondoid components having a boiling point both below and above the lowest boiling point higher diamondoid component selected for recovery as well as one or more lower diamondoid components. These feedstocks will usually contain a mixture of higher diamondoids. Depending upon which higher diamondoids are selected, some of these higher diamondoids may have boiling points below the selected diamondoid's boiling point. Typically, the lowest boiling point higher diamondoid component selected for recovery will have a boiling point of greater than about 335° C. In typical feedstocks, the concentration of lower diamondoids to higher diamondoids is generally about 260:1 or higher. Moreover, as illustrated in FIGS. 20 and 21, typical feedstocks comprising higher diamondoid components also comprise nondiamondoid components.

In such feedstocks, selected higher diamondoid components often cannot be effectively recovered directly from the feedstock because of their low concentrations relative to the nonselected components. Accordingly, the processes of this invention may entail removal of a sufficient amount of these contaminants from the feedstock under conditions to provide a treated feedstock from which the selected higher diamondoid components can be recovered.

In one embodiment, the removal of contaminants includes distillation of the feedstock to remove nondiamondoid components as well as lower diamondoid components and in some cases other nonselected higher diamondoids having boiling points less than that of the lowest boiling point higher diamondoid component selected for recovery.

In a particularly preferred embodiment, the feedstock is distilled to provide cuts above and below about 335° C., atmospheric equivalent boiling point and, more preferably, above and below about 345° C. atmospheric equivalent boiling point. In either instance, the lower cuts, which are enriched in lower diamondoids and low boiling point nondiamondoid components are taken overhead and discarded and the higher boiling cut, which is enriched in higher diamondoids, is retained. It is understood, of course, that the temperature for the cut point during distillation is a function of pressure and that the above temperatures are atmospheric equivalents. A reduced pressure will result in a lower distillation temperature to achieve the same cut point whereas an elevated pressure will result in a higher distillation temperature to achieve the same cut point. The correlation of pressure/temperature from atmospheric distillation to either reduced pressure or elevated pressure distillation is well within the skill of the art.

Distillation can be operated to fractionate the feedstocks and provide several cuts in a temperature range of interest to provide the initial enrichment of the selected higher diamondoids or groups of selected higher diamondoids. The cuts, which are enriched in selected one or more diamondoids or a particular diamondoid component of interest, are retained and may require further purification. The following Table illustrates representative fractionation points (atmospheric equivalent boiling points) that may be used to enrich various higher diamondoids in overheads. In practice it may be advantageous to make wider temperature range cuts which would often contain groups of higher diamondoids which could be separated in subsequent separation steps.

| | Fractionation Points | | | | | |
|---|---|---|---|---|---|---|
| | Most Preferred | | Preferred | | Useful | |
| Higher Diamondoid | Lower Cut Temperature (° C.) | Higher Cut Temperature (° C.) | Lower Cut Temperature (° C.) | Higher Cut Temperature (° C.) | Lower Cut Temperature (° C.) | Higher Cut Temperature (° C.) |
| Tetramantanes | 349 | 382 | 330 | 400 | 300 | 430 |
| Pentamantanes | 385 | 427 | 360 | 450 | 330 | 490 |
| Cyclohexamantanes | 393 | 466 | 365 | 500 | 330 | 550 |
| Hexamantanes | 393 | 466 | 365 | 500 | 330 | 550 |
| Heptamantanes | 432 | 504 | 395 | 540 | 350 | 600 |
| Octamantanes | 454 | 527 | 420 | 560 | 375 | 610 |
| Nonamantanes | 463 | 549 | 425 | 590 | 380 | 650 |
| Decamantanes | 472 | 571 | 435 | 610 | 390 | 660 |
| Undecamantanes | 499 | 588 | 455 | 625 | 400 | 675 |

It shall be understood that substituted higher diamondoids may accordingly shift these preferred temperatures to higher temperatures due to the addition of substituent groups. Additional temperature refinements will allow for higher purity cuts for the diamondoid of interest. FIG. 31 provides further illustrations of how fractionation can provide cuts enriched in individual or multiple higher diamondoid components.

It will be further understood that fractionation can be stopped before a selected higher diamondoid is taken overhead. In this case the higher diamondoid can be separated from the fractionation bottoms.

Other processes for the removal of lower diamondoids, unselected higher diamondoids, if any, and/or hydrocarbonaceous nondiamondoid components include, by way of example only, size separation techniques, evaporation either under normal or reduced pressure, crystallization, chromatography, well head separators, reduced pressure and the like. For example, lower diamondoids can be preferentially removed from feedstocks using a variety of techniques. First of all, adamantane and diamantane dissolved in deep gases, may crystallize during commercial gas and liquids production due to a drop in pressure. Commercially available well head separators effectively remove lower diamondoids from such feedstocks to avoid scaling problems in oil and gas production equipment. Other removal processes can utilize the larger sizes of the higher diamondoids to effect separation of lower diamondoids therefrom. For example, size separation techniques using membranes will allow a feedstock retained in the membrane to selectively pass lower diamondoids across the membrane barrier provided that the pore size of the membrane barrier is selected to differentiate between compounds having the size of higher diamondoid components as compared to lower diamondoid components. The pore size of molecular sieves such as zeolites and the like can also be used to effect size separation.

In a preferred embodiment, the removal process provides for a treated feedstock having a ratio of lower diamondoid components to higher diamondoid components of no greater than 9:1; more preferably, no greater than 2:1; and even more preferably, the ratio is no greater than 1:1. Even more preferably, after removal of the lower diamondoid component(s) from the feedstock, at least about 10%, more preferably at least 50% and still more preferably at least 90% of the higher diamondoid components are retained in the feedstock as compared to that amount found in the feedstock prior to the removal.

When recovery of hexamantane and higher diamondoid components is desired, the feedstock will also generally be subjected to pyrolysis to effect removal of at least a portion of the hydrocarbonaceous nondiamondoid components from the feedstock. The pyrolysis effectively concentrates the amount of higher diamondoids in the pyrolytically treated feedstock thereby rendering their recovery possible.

Pyrolysis is effected by heating the feedstock under vacuum conditions or in an inert atmosphere, at a temperature of at least about 390° C. and, preferably, from about 400 to about 500° C., more preferably from about 400 to about 450° C., and especially 410 to 430° C.; for a period of time to effect pyrolysis of at least a portion of the nondiamondoid components of the feedstock. The specific conditions employed are selected such that recoverable amounts of higher diamondoid components are retained in the feedstock. The selection of such conditions is well within the skill of the art.

Preferably, pyrolysis is continued for a sufficient period and at a sufficiently high temperature to thermally degrade at least about 10% of the nondiamondoid components (more preferably at least about 50% and even more preferably at least about 90%) from the pyrolytically treated feedstock based on the total weight of the nondiamondoid components in the feedstock prior to pyrolysis.

In yet another preferred embodiment, after pyrolysis of the feedstock, at least about 10%, more preferably at least about 50%, and still more preferably at least about 90% of the higher diamondoid components are retained in the feedstock after pyrolytic treatment compared to that amount found in the feedstock prior to pyrolytic treatment.

In a preferred embodiment, removal of lower diamondoids and low boiling point hydrocarbonaceous nondiamondoid components from the feedstock precedes pyrolytic treatment. However, it is understood, that the order of these procedures can be inverted such that pyrolysis occurs prior to removal of lower diamondoids from the feedstock.

The pyrolysis procedure, while a preferred embodiment, is not always necessary. This arises because the concentration of higher diamondoid can be sufficiently high in certain feedstocks that the treated feedstock (after removal of the lower diamondoid components) can be used directly in purification techniques such as chromatography, crystallization, etc. to provide higher diamondoid components. However, when the concentration or purity of higher diamondoid components in the feedstock is not at the level to effect such a recovery, then a pyrolytic step should be employed.

Even when pyrolysis is employed, it is preferred to further purify the recovered feedstock using one or more purification techniques such as chromatography, crystallization, thermal diffusion techniques, zone refining, progressive recrystalization, size separation and the like. In a particularly preferred process, the recovered feedstock is first subjected to gravity column chromatography using silver nitrate impregnated silica gel followed by HPLC using two different columns of differing selectivities to isolate the target diamondoids; and crystallization to provide crystals of pure target higher diamondoids. Where higher diamondoid concentrations are not high enough for crystallization to occur, further concentration by, for example, preparative capillary gas chromatography, may be necessary.

Compositions

The above processes provide novel higher diamondoid compositions. For example, in one embodiment, these processes provide a composition comprising at least tetramantane and pentamantane components wherein said composition comprises at least about 10 weight percent tetramantane components and at least about 0.5 weight percent pentamantane components based on the total amount of diamondoid components present. Alternatively, the compositions of this invention comprise at least about 10 weight percent tetramantane components and at least about 0.5 weight percent pentamantane components based on the total weight of the composition.

In a preferred embodiment, the composition comprises at least tetramantane and pentamantane components wherein said composition comprises at least about 25 weight percent tetramantane components and at least 1 weight percent pentamantane components based on the total amount of diamondoid component present; and, even more preferably, at least about 50 weight percent tetramantane components and at least 1 weight percent pentamantane components based on the total amount of diamondoid component present.

In another preferred embodiment, the composition comprises at least tetramantane and pentamantane components wherein said composition comprises at least about 25 weight percent tetramantane components and at least 1 weight percent pentamantane components based on the total weight of the composition; and, even more preferably, at least about 50 weight percent tetramantane components and at least 1 weight percent pentamantane components based on the total weight of the composition.

In addition to the tetramantane and pentamantane components found in these compositions, the compositions preferably further comprise hexamantane components and, even more preferably, one or more of heptamantane, octamantane, nonamantane, decamantane, undecamantane components. More preferably, the hexamantane components found in any such composition do not include the fully condensed cyclohexamantane of the formula $C_{26}H_{30}$ and having a molecular weight of 342.

Further purification of these compositions will lead to compositions which comprise at least about 50% or more of tetramantane components (either as individual isomers or as a mixture of tetramantane isomers), pentamantane components (either as individual isomers or as a mixture of pentamantane isomers), hexamantane components (either as individual isomers or as a mixture of hexamantane isomers), heptamantane components (either as individual isomers or as a mixture of heptamantane isomers), octamantane components (either as individual isomers or as a mixture of octamantane isomers), nonamantane components (either as individual isomers or as a mixture of nonamantane isomers) decamantane components (either as individual isomers or as a mixture of decamantane isomers) and the like.

The compositions described above contain non-ionized higher diamondoid components.

Utility

The processes of this invention provide for compositions enhanced in higher diamondoids. These higher diamondoids are useful in micro- and molecular-electronics and nanotechnology applications. In particular, the rigidity, strength, stability, thermal conductivity, variety of structural forms and multiple attachment sites shown by these molecules makes possible accurate construction of robust, durable, precision devices with nanometer dimensions.

In addition, these higher diamondoids can also be used in a high quality lubricating fluid which exhibits a high Viscosity Index and a very low pour point.[13] When so employed, these fluids comprise a fluid of lubricating viscosity and from about 0.1 to 10 weight percent diamondoids.

Still further, these higher diamondoids can be used as high density fuels in the manner described by Chung, et al.[14], incorporated herein by reference.

The following examples are offered to illustrate this invention and are not to be construed in any way as limiting the scope of this invention. Unless otherwise stated, all temperatures are in degrees Celsius.

EXAMPLES

As used herein and in the Figures, the following abbreviations have the following meanings. Any abbreviation not defined below has its generally accepted meaning.

| | |
|---|---|
| API = | American Petroleum Institute |
| atm eqv = | atmospheric equivalent |
| btms = | bottoms |
| EOR Traps = | end of run traps |
| fid = | flame ionization detector |
| g = | grams |
| GC = | gas chromatography |
| GC/MS = | gas chromatography/mass spectroscopy |
| h = | hour |
| HPLC = | high performance liquid chromatography |
| HYD RDG = | hydrometer reading |
| L = | liter |
| min = | minute |
| mL = | milliliters |
| mmol = | millimols |
| N = | normal |
| pA = | pico amps |
| ppb = | parts per billion |
| ppm = | parts per million |
| RI = | refractive index |
| SIM DIS = | simulated distillation |
| ST = | start |
| TIC = | total ion current |

-continued

| | |
|---|---|
| TLC = | thin layer chromatography |
| VLT = | vapor line temperature |
| VOL PCT = | volume percent |
| v/v = | volume to volume |
| wt = | weight |
| WT PCT = | weight percent |

Introduction

The following higher diamondoid components were isolated and crystallized: all of the tetramantanes from both Feedstocks A and B, all pentamantanes (mol. wt. 344) isolated from Feedstock B; two hexamantane crystals (mol. wt. 396) isolated from Feedstock B; and, two heptamantane crystals (mol. wt. 394) isolated from Feedstock B, octamantane crystal (mol. wt 446) isolated from Feedstock B. As well as a nonamantane crystal (mol. wt. 498) and a decamantane crystal (mol. wt. 456) isolated from Feedstock B. The other higher diamondoid components could also be isolated using the procedures set forth in these examples.

Figure 34:
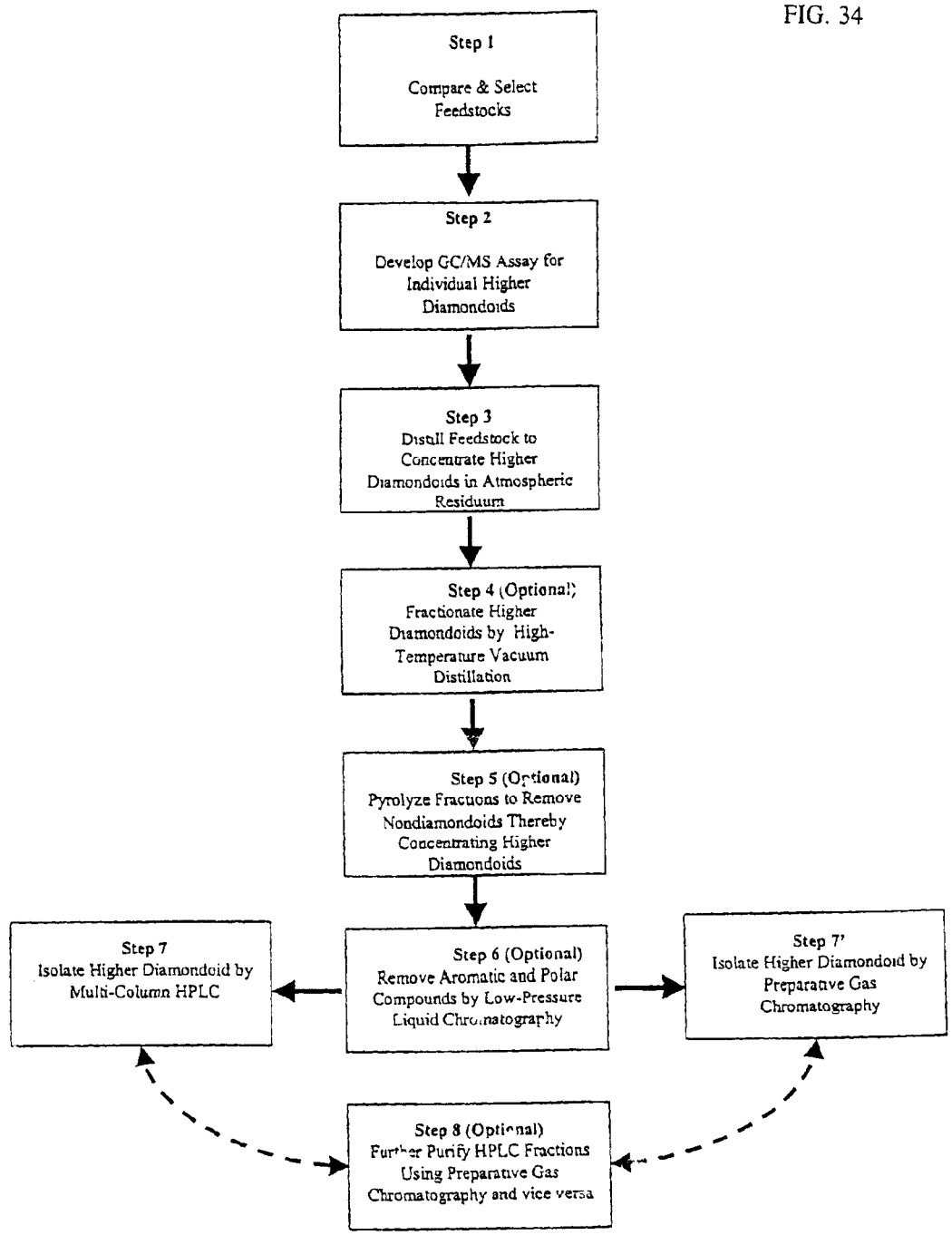
FIG. 34 gives a flow chart representing the various steps used in the isolation of higher diamondoid-containing fractions and individual higher diamondoid components. Note that the steps can in some cases be used in a different sequence and possibly skipped as discussed in the Examples.

The steps used in the various Examples are shown schematically in FIG. 34.

Example 1 describes a most universal route for isolating higher diamondoids components which can be applied to all feedstocks. This process uses HPLC (Step 7, FIG. 34) as its final isolation step.

Example 2 describes a variation of the process of Example 1 in which preparative gas chromatography (Step 7, FIG. 34) replaces HPLC as the final isolation step.

Example 3 describes a variation of the process of Example 1 in which the pyrolysis (Step 5, FIG. 34) is omitted. As shown optionally in FIG. 34, the liquid chromatographic step (Step 6, FIG. 34) is also omitted. These variations generally have applicability only with selected feedstocks and generally when tetramantanes, pentamantane and cyclohexamantane are the target higher diamondoids.

Example 4 describes yet another process variation in which the final products of Examples 1 and 3 are subjected to preparative gas chromatography purification to give further separation of higher diamondoid components (Step 8, FIG. 34).

Example 5 describes pyrolysis of Feedstock B distillate fraction #5.

Example 6 describes removal of nondiamondoids using pyrolysis during isolation of tetramantanes.

Example 7 describes the isolation of tetramantanes using HPLC.

Example 8 describes analysis of feedstocks, which are rich in higher diamondoids.

Example 9 describes the enrichment and isolation of pentamantane components using gas chromatography.

Example 10 shows the presence of heptamantanes, octamantanes and decamantanes in pyrolysis products.

Examples 11A and B and C describe the enrichment and isolation of heptamantane components.

Examples 12A and B describe the enrichment and isolation of octamantane components.

Examples 13A and B describe the enrichment and isolation of nonamantanes components.

Examples 14A and B describe the enrichment and isolation of decamantane components.

Example 15 describes the enrichment and isolation of undecamantane components.

It will be understood that it is possible to vary the order of the various distillation, chromatography and pyrolysis steps, although the order set forth in Example 1 has given the best results.

Example 1

This Example has seven steps (see Flow Chart in FIG. 34).

Step 1. Feedstock selection
Step 2. GCMC assay
Step 3. Feedstock atmospheric distillation
Step 4. Vacuum fractionation of atmospheric distillation residue
Step 5. Pyrolysis of isolated fractions
Step 6. Removal of aromatic and polar nondiamondoid components
Step 7. Multi-column HPLC isolation of higher diamondoids
  a) First column of first selectivity to provide fractions enriched in specific higher diamondoids.
  b) Second column of different selectivity to provide isolated higher diamondoids.

This example is written in terms of isolating several hexamantanes. As will be shown in Examples 5–15 it can be easily adapted to isolate the other higher diamondoids.

Step 1—Feedstock Selection

Figure 2:
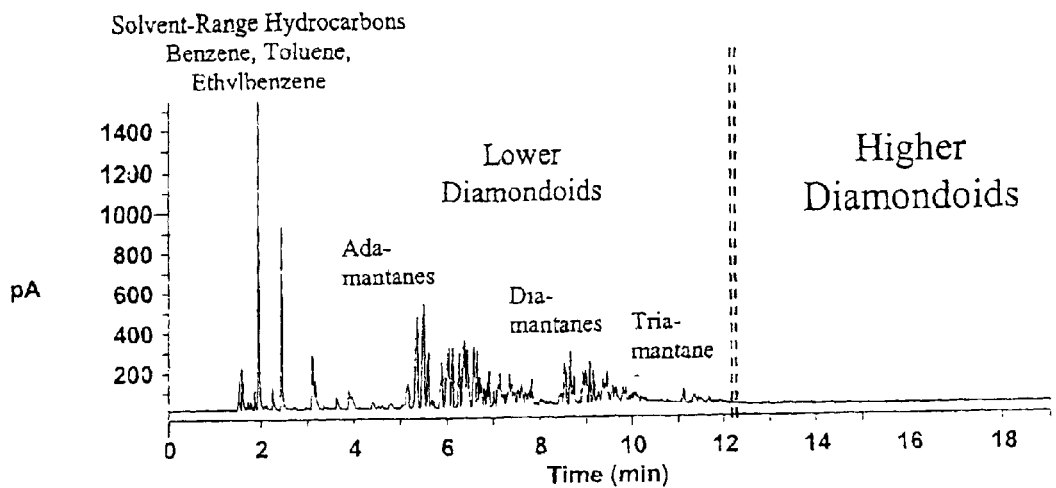
FIG. 2 illustrates the gas chromatogram of a gas condensate feedstock; one of the original feedstocks used in the Examples (Feedstock A).
Figure 3:
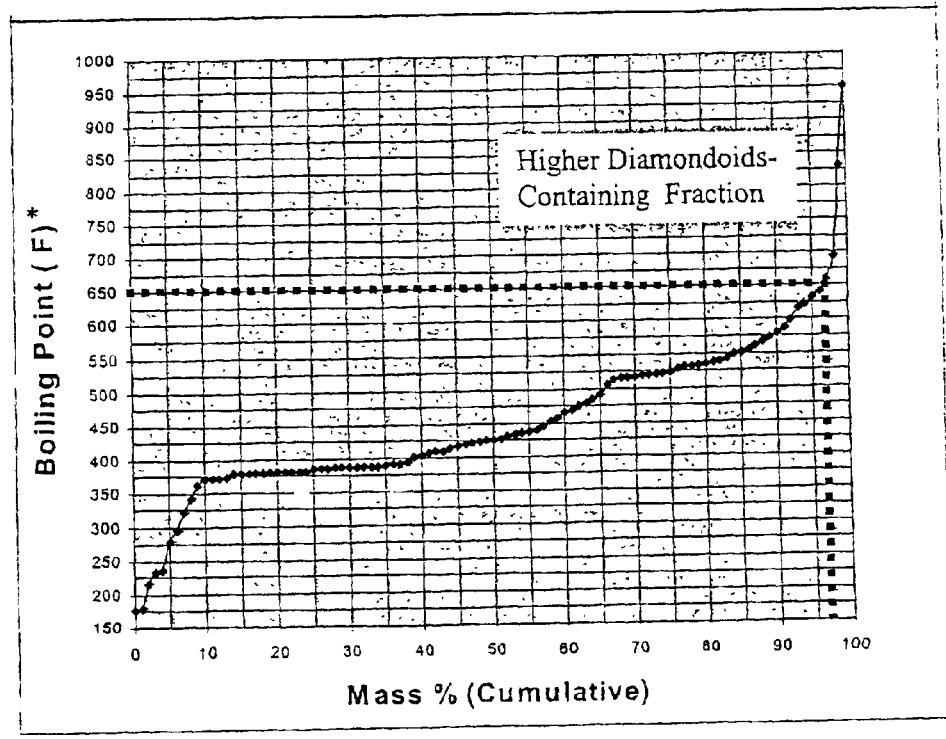
FIG. 3 illustrates a simulated distillation profile of a gas condensate feedstock containing petroleum byproducts used in the Examples (Feedstock B). Boiling points depicted are atmospheric equivalents.
Figure 4:
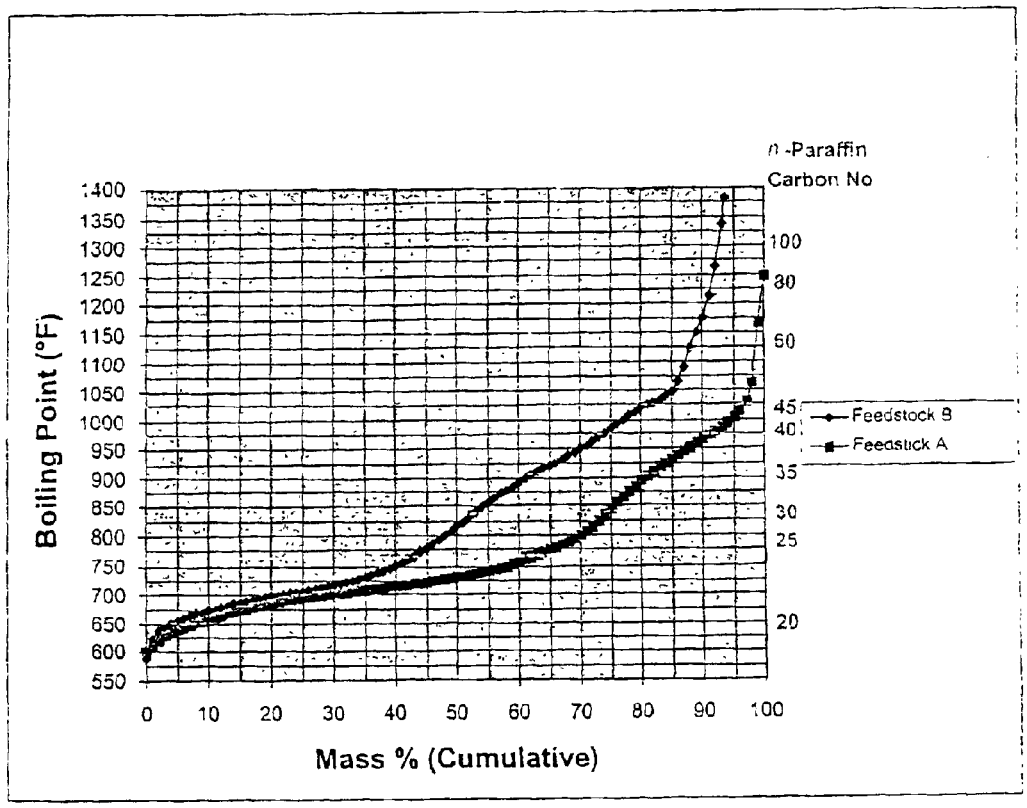
FIG. 4 illustrates a high temperature simulated distillation profile of atmospheric residue of diamondoid rich gas condensates; Feedstock A and Feedstock B. This Figure also illustrates the n-paraffin carbon number atmospheric equivalent boiling point.
Figure 5:
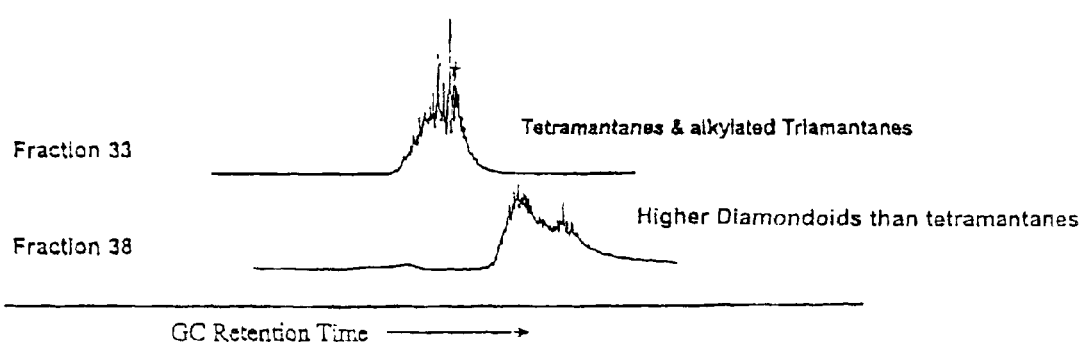
FIG. 5 illustrates gas chromatographic profiles of distillate fractions containing tetramantanes and other higher diamondoids from a gas condensate, Feedstock A.

Suitable starting materials were obtained. These materials included a gas condensate, Feedstock A (FIG. 2), and a gas condensate containing petroleum components, Feedstock B. Although other condensates, petroleums, or refinery cuts and products could have been used, these two materials were chosen due to their high diamondoid concentration, approximately 0.3 weight percent higher diamondoids, as determined by GC and GC/MS. Both feedstocks were light colored and had API gravities between 19 and 20° API.

Step 2—GC/MS Assay

Feedstock A was analyzed using gas chromatography/mass spectrometry to confirm the presence of target higher diamondoids and to provide gas chromatographic retention times for these target materials. This information is used to track individual target higher diamondoids through subsequent isolation procedures. FIG. 35A is a table that lists typical GC/MS assay information for the hexamantanes (GC retention times, mass spectral molecular ion (M+) and base peak). This table (FIG. 35A) also contains similar GC/MS assay information for other higher diamondoids. While relative GC retention times are approximately constant, non-referenced GC retentions vary with time. It is recommended that GC/MS assay values be routinely updated especially when GC retention time drift is detected.

Step 3—Feedstock Atmospheric Distillation

A sample of Feedstock B was distilled into a number of fractions based on boiling points to separate the lower boiling point components (nondiamondoids and lower diamondoids) and for further concentration and enrichment of particular higher diamondoids in various fractions. The yields of atmospheric distillate fractions of two separate samples of Feedstock B are shown in Table 1, below and are contrasted to simulated distillation yields. As seen from Table 1, the simulated distillation data is in agreement with the actual distillation data. The simulated distillation data were used to plan subsequent distillation processes.

TABLE 1

Yields of Atmospheric Distillation Fractions from Two Separate Runs of Feedstock B

| Cut (° F.) | Sim Dis Est.'d Yields (Wt %) | Feedstock B (Run 2) Yields (Wt %) | Difference |
|---|---|---|---|
| To 349 | 8.0 | 7.6 | 0.4 |
| 349 to 491 | 57.0 | 57.7 | −0.7 |
| 491 to 643 | 31.0 | 30.6 | 0.4 |
| 643 and higher | 4.0 | 4.1 | −0.1 |

| Cut (° F.) | Sim Dis Est.'d Yields (Wt %) | Feedstock B (Run 1) Yields (Wt %) | Difference |
|---|---|---|---|
| To 477 | 63.2 | 59.3 | 3.9 |
| 477 to 515 | 4.8 | 7.3 | −2.5 |
| 515 to 649 | 28.5 | 31.2 | −2.7 |
| 649 and higher | 3.5 | 2.1 | 1.4 |

Figure 12:
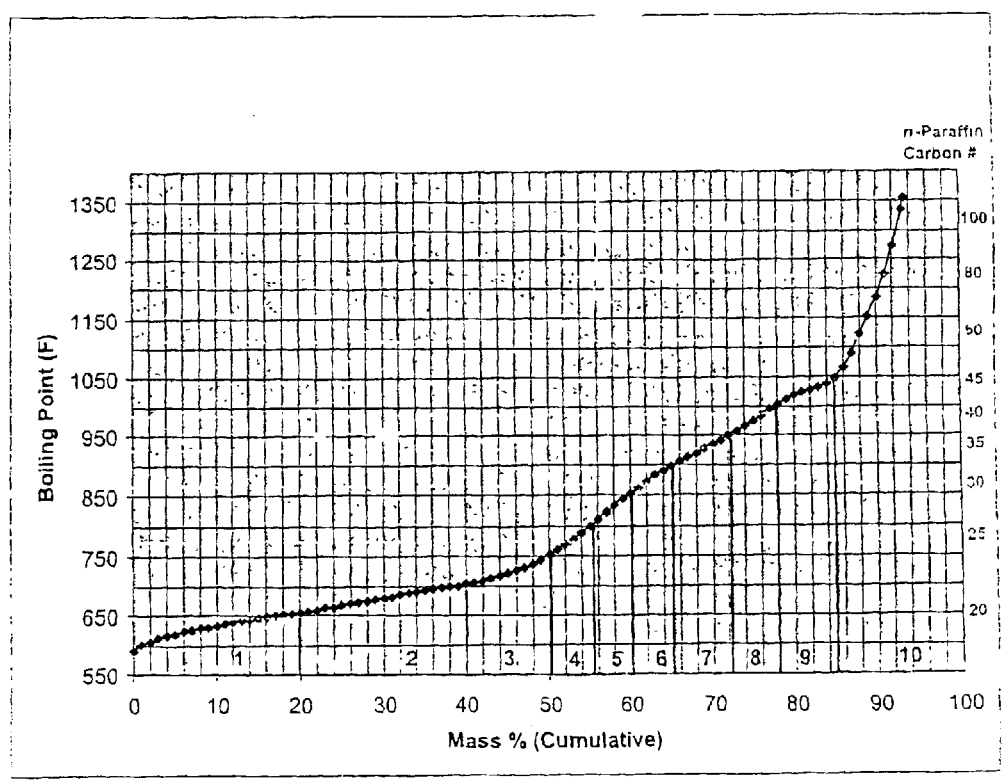
FIG. 12 illustrates a high temperature simulated distillation profile of Feedstock B using the atmospheric distillation 650° F.+ bottoms as feedstock. This FIG. also illustrates the targeted cut points (1–10) for higher diamondoid isolations.

Step 4—Fractionation of Atmospheric Distillation Residue by Vacuum Distillation The resulting Feedstock B atmospheric residium from Step 3 (comprising 2–4 weight percent of the original feedstock) was distilled into fractions containing higher diamondoids as shown in FIGS. 12 and 31). The feed to this high temperature distillation process was the atmospheric 650° F.+ bottoms. Complete Feedstock B distillation reports are given in Tables 2A and 2B. Tables 3A and 3B illustrate the distillation reports for Feedstock B 650° F.+ distillation bottoms.

TABLE 2A

Distillation Report for Feedstock B

Feedstock B
Column Used: Clean 9" x 1.4" Protruded Packed

| CUT | VAPOR TEMP ST–END | | | DISTILLATION RECORD WEIGHT G | VOLUME ml @ 60° F. | API 60/60 | DENSITY @ 60° F. | NORMALIZED WT PCT | VOL PCT | ACTUAL WT PCT | VOL PCT |
|---|---|---|---|---|---|---|---|---|---|---|---|
| 1 | 226 | – | 349 | 67.0 | 80 | 38.0 | 0.8348 | 7.61 | 8.54 | 7.39 | 8.26 |
| 2 | 349 | – | 491 | 507.7 | 554 | 22.8 | 0.9170 | 57.65 | 59.12 | 55.98 | 57.23 |
| 3 | 491 | – | 643 | 269.6 | 268 | 9.1 | 1.0064 | 30.62 | 28.60 | 29.73 | 27.69 |
| COL HOLDUP | | | | 0.2 | 0 | 6.6 | 1.0246 | 0.02 | 0.00 | 0.02 | 0.00 |
| BTMS | 643 | + | | 36.1 | 35 | 6.6 | 1.0246 | 4.09 | 3.74 | 3.98 | 3.62 |
| EOR TRAPS | | | | 0.0 | 0 | | | 0.00 | 0.00 | | 0.00 |
| TOTALS | | | | 880.6 | 937 | | | 100.00 | 100.00 | 97.09 | 96.80 |
| LOSS | | | | 26.4 | 31 | | | | | 2.91 | 3.20 |
| FEED | | | | 907.0 | 968 | 19.5 | 0.9371 | | | 100.00 | 100.00 |
| BACK CALCULATED API AND DENSITY | | | | | | 19.1 | 0.9396 | | | | |

TABLE 2B

Distillation Report for Feedstock B

Feedstock B  
Column Used: Clean 9" x 1.4" Protruded Packed

| VLT | ATM EQV. | POT | PRESSURE TORR | REFLUX RATIO | CUT NO | VOLUME ml @ 60° F. | WEIGHT G | HYD RDG | TEMP ° F. | 60° F. |
|---|---|---|---|---|---|---|---|---|---|---|
| | | | | | | | TEMPERATURE DEGREES F. — VAPOR | | API GRAVITIES OBSERVED | |
| 93 | 225.8 | 262 | 50.000 | 3:1 | | START OVERHEAD | | | | |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |
| | | | | | | | | | | |
| | Cut 2 looks Milky, White crystals form in Run Down Line. Heat Lamp applied to drip tube. Cool to transfer btms to smaller flask. | | | | | | | | | |
| 208 | 437.7 | 323 | 10.000 | 3:1 | | START OVERHEAD | | | | |
| 378 | 643.3 | 550 | 10.000 | 3:1 | 3 | 268 | 269.6 | 9.9 | 75.0 | 9.1 |
| | Shutdown due to dry pot | | | | | | | | | |
| | | | END OF RUN TRAPS | | | 0 | 0.0 | | | |
| | | | VOLUME DISTILLED | | | 902 | | | | |
| | | | COLUMN HOLDUP | | | 0 | 0.2 | 0.0 | 0.0 | 6.6 |
| | | | BOTTOMS | | | 35 | 36.1 | 7.2 | 72.0 | 6.6 |
| | | | RECOVERED | | | 937 | 880.6 | | | |
| | | | FEED CHARGED | | | 968 | 907.0 | 20.7 | 80.0 | 19.5 |
| | | | LOSS | | | 31 | 26.4 | | | |

TABLE 3A

Vacuum Distillation Report for Feedstock B

Feedstock B - Atmospheric distillation resid 650° F. + bottoms  
Column Used: Sarnia Hi Vac

| VLT | ATM EQV. | POT | PRESSURE TORR | REFLUX RATIO | CUT NO | VOLUME ml 60° F. | WEIGHT G | HYD RDG | TEMP ° F. | 60° F. |
|---|---|---|---|---|---|---|---|---|---|---|
| 315 | 601.4 | 350 | 5.000 | | | START OVERHEAD | | | | |
| 344 | 636.8 | 382 | 5.000 | | | 300 | READING | | | |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |
| | Shut down distillation to check pot temperature limits with customer. (Drained trap material 5.3 grams) | | | | | | | | | |
| 472 | 935.7 | 576 | 0.222 | | | START OVERHEAD | | | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |
| | Drained remaining trap material of 16.5 grams (~4 grams of water) | | | | | | | | | |
| | | | MID AND END OF RUN TRAPS | | | 20 | 17.8 | (mathematically combined) | | |
| | | | VOLUME DISTILLED | | | 2701 | | | | |
| | | | COLUMN HOLDUP | | | 4 | 4.0 | 0.0 | 0.0 | 3.4 |
| | | | BOTTOMS | | | 593 | 621.8 | 11.0 | 214.0 | 3.4 |
| | | | RECOVERED | | | 3298 | 3311.7 | | | |
| | | | FEED CHARGED | | | 3298 | 3326.3 | 18.0 | 234.0 | 8.6 |
| | | | LOSS | | | −5 | 14.6 | | | |

TABLE 3B

Distillation Report for Feedstock B-btms

Feedstock B - Atmospheric distillation resid 650° F. + bottoms
Column Used: Sarnia HiVac

| CUT | VAPOR TEMP ST–END | | | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|---|---|
| 1 | 601 | – | 656 | 666.4 | 639 | 4.1 | 1.0435 | 20.12 | 19.38 | 20.03 | 19.40 |
| 2 | 656 | – | 702 | 666.9 | 646 | 5.6 | 1.0321 | 20.14 | 19.59 | 20.05 | 19.62 |
| 3 | 702 | – | 752 | 334.3 | 330 | 8.3 | 1.0122 | 10.09 | 10.01 | 10.05 | 10.02 |
| 4 | 752 | – | 800 | 167.7 | 173 | 14.5 | 0.9692 | 5.06 | 5.25 | 5.04 | 5.25 |
| 5 | 800 | – | 852 | 167.3 | 181 | 21.7 | 0.9236 | 5.05 | 5.49 | 5.03 | 5.50 |
| 6 | 852 | – | 900 | 167.1 | 181 | 21.9 | 0.9224 | 5.05 | 5.49 | 5.02 | 5.50 |
| 7 | 900 | – | 950 | 238.4 | 257 | 21.2 | 0.9267 | 7.25 | 7.79 | 7.17 | 7.80 |
| 8 | 950 | – | 976 | 85.4 | 91 | 18.9 | 0.9408 | 2.58 | 2.76 | 2.57 | 2.76 |
| 9 | 976 | – | 1000 | 80.8 | 85 | 18.2 | 0.9452 | 2.44 | 2.58 | 2.43 | 2.58 |
| 10 | 1000 | – | 1026 | 93.8 | 98 | 16.9 | 0.9535 | 2.83 | 2.97 | 2.82 | 2.98 |
| COL HOLDUP | | | | 4.0 | 4 | 3.4 | 1.0489 | 0.12 | 0.12 | 0.12 | 0.12 |
| BTMS | 1026 | + | | 621.8 | 593 | 3.4 | 1.0489 | 18.78 | 17.98 | 18.69 | 18.01 |
| EOR TRAPS | | | | 17.8 | 20 | | | 0.54 | 0.61 | 0.54 | 0.61 |
| TOTALS | | | | 3311.7 | 3298 | | | 100.00 | 100.00 | 99.56 | 100.15 |
| LOSS | | | | 14.6 | –5 | | | | | 0.44 | –0.15 |
| FEED | | | | 3326.3 | 3293 | 8.6 | 1.0100 | | | 100.00 | 100.00 |
| BACK CALCULATED API & DENSITY | | | | | | 9.4 | 1.0039 | | | | |

TABLE 4

Elemental Composition of Feedstock B

Analyses on Feedstock B 650 + F Resid

| Measured | Value |
|---|---|
| Nitrogen | 0.991 wt % |
| Sulfur | 0.863 wt % |
| Nickel | 8.61 ppm |
| Vanadium | <0.2 ppm |

Table 4 illustrates the partial elemental composition of Feedstock B atmospheric distillation (650° F.) residue including some of the identified impurities. Table 4 displays the weight percent nitrogen, sulfur, nickel and vanadium in Feedstock B atmospheric distillation residue. Subsequent steps remove these materials.

Step 5—Pyrolysis of Isolated Fractions

A high-temperature reactor was used to pyrolyze and degrade a portion of the nondiamondoid components in various distillation fractions obtained in Step 4 (FIG. 34) thereby enriching the diamondoids in the residue. The pyrolysis process was conducted at 450° C. for 19.5 hours. The gas chromatogram (FID) of fraction #6 (Table 3B) is shown in FIG. 20A. FIG. 20B is the chromatogram for the product of pyrolysis. A comparison of these chromatograms shows that pyrolysis has removed major nondiamondoid hydrocarbons and has significantly increased the higher diamondoid concentration, especially the hexamantanes. A 500 mL PARR® reactor from PARR Instrument Company, Moline, Ill. was used in this pyrolysis step.

Step 6—Removal of Aromatic and Polar Nondiamondoid Components

The pyrolysate produced in Step 5 was passed through a silica-gel gravity chromatography column (using cyclohexane elution solvent) to remove polar compounds and asphaltenes (Step 6, FIG. 34). The use of a silver nitrate impregnated silica gel (10 weight percent AgNO$_3$) provides cleaner diamondoid-containing fractions by removing the free aromatic and polar components. While it is not necessary to use this chromatographic aromatic separation method, it facilitates subsequent steps.

Step 7—Multi-column HPLC Isolation of Higher Diamondoids

An excellent method for isolating high-purity higher diamondoids uses two or more HPLC columns of different selectivities in succession.

The first HPLC system consisted of two Whatman M20 10/50 ODS columns operated in series using acetone as mobile phase at 5.00 mL/min. A series of HPLC fractions were taken (see FIG. 32). Fractions 36 and 37 were combined and taken for further purification on a second HPLC system. This combined fraction (36 and 37) contained hexamantanes #7, #11 and #13. (FIG. 32, also see FIG. 35B).

Further purification of this combined ODS HPLC fraction was achieved using a Hypercarb stationary phase HPLC column having a different selectivity in the separation of various hexamantanes than the ODS column discussed above. FIG. 33 shows elution times of the individual hexamantanes on the Hypercarb HPLC column (with acetone as a mobile phase).

The differences in elution times and elution order of hexamantanes on ODS and Hypercarb HPLC columns are seen by comparing these two FIGS. 32 and 33. For example, Hexamantanes #11 and #13 elute together on the ODS HPLC system (FIG. 32) but in separate fractions (fractions 32 and 27, respectively) on the Hypercarb system (FIG. 33).

The different elution orders and times of selected higher diamondoids on these two systems can be used to separate co-eluting higher diamondoids. It can also be used to remove impurities. Using this method on combined ODS HPLC fractions 36 & 37, appropriate Hypercarb HPLC fractions were taken thus providing high-purity hexamantane #13 (FIG. 33). Other ODS HPLC fractions and Hypercarb HPLC cut points could be used to isolate the remaining hexamantanes. This isolation strategy is also applicable to the other higher diamondoids although elution solvent compositions can vary.

The ODS and Hypercarb columns can also be used in reverse order for these isolations. By using similar methodology as above, i.e. fractionating hexamantane-containing ODS fractions using the Hypercarb or other suitable column and collecting at corresponding elution times can lead to the isolation of the remaining hexamantanes in high purity. This is also true of the other higher diamondoids from tetramantanes to undecamantanes, including substituted forms.

Example 2

Steps 1, 2, 3, 4, 5 and 6 of Example 1 were repeated (FIG. 34). The following variation of Step 7 was then carried out. Step 7':

A two-column preparative capillary gas chromatograph was used to isolate hexamantanes from the product of Example 1, Step 6. The cut times for the hexamantanes were set for the first preparative capillary the GC column, methyl silicone DB-1 equivalent, using the retention times and patterns from GC/MS assay (Example 1, Step 2). The results are shown in FIG. 37A, two cuts identified as "peaks cut and sent to column 2", were taken which contains two of the hexamantane components from Feedstock B.

The first column was used to concentrate the higher diamondoids, such as hexamantanes by taking cuts that were then sent to the second column (see FIG. 37B illustrated for hexamantane #2 and #8). The second column, phenyl-methyl silicone, a DB-17 equivalent, further separated and purified the hexamantanes and then was used to isolate peaks of interest and retain them in individual traps (traps 1–6). GC trap fraction 1 contained crystals of hexamantane #2. GC trap fraction 3 contained crystals of hexamantane #8. Subsequent GC/MS analysis of trap #1 material showed it to be high purity hexamantane #2 based upon the GC/MS assay of Step 2. Similarly, the GC/MS analysis of trap #3 material showed it to be primarily hexamantane #8 (FIGS. 28B and 28C). Both hexamantane #2 and #8 (FIG. 28A) formed crystals. This procedure could be repeated to isolate the other hexamantanes. This is also true of the other higher diamondoids.

Example 3

Steps 1, 2, 3, and 4 (FIG. 34) of Example 1 were repeated using Feedstock A. Feedstock A is especially low in non-diamondoids in the atmospheric residue fraction recovered in Step 4. The pyrolysis Step (5) of Example 1 may be omitted especially when the higher diamondoids being sought are tetramantanes, pentamantanes and cyclohexamantane. In this case the fractions removed in Step 4 go directly to Steps 6 and 7 in Example 1 or directly to Step 7 in Example 2 (FIG. 34). This process variation can be applied to lower-boiling tetramantane-containing fractions of Feedstock B as well. However, pyrolysis is highly desirable where significant nondiamondoid components are present.

A fraction corresponding in cutpoint to fraction #1 of Step 4 (see distillation Table 3, Example 1 and FIG. 12) was taken from this feedstock. This fraction was further fractionated by preparative capillary gas chromatography similar to the processing shown in Step 7' of Example 2 (FIG. 34).

Figure 6:
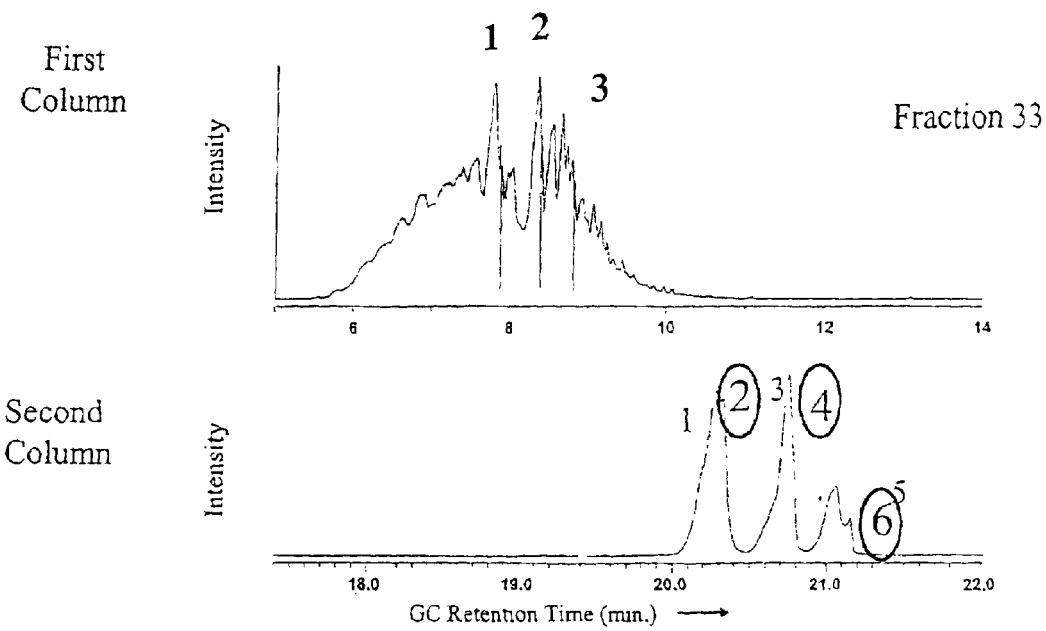
FIG. 6 illustrates the preparative capillary gas chromatographic data for tetramantane isolations. The first column shows cuts made on distillate fraction 33, Feedstock A. The bold face numbers refers to peaks of the tetramantanes. The second column shows peaks isolated and sent to the traps. The circled numbered peaks (2, 4, and 6) are the tetramantanes. It is noted that both enantiomers of the optically active tetramantane are contained within one of these peaks.

A two-column preparative capillary gas chromatograph was then used to isolate the target tetramantanes from the distillate fraction cleaned-up by column chromatography (Step 6, FIG. 34). Using the retention times and patterns from the GC/MS assay (from Step 2 of Example 1), the cut times for the target diamondoids (e.g., tetramantanes) were set for the first preparative capillary GC column, methyl silicone DB-1 equivalent. The results are shown on FIG. 6A identified as cuts 1, 2 and 3.

The first column was used to concentrate the target diamondoids (e.g., tetramantanes) by taking cuts that were then sent to the second column (phenyl-methyl silicone, a DB-17 equivalent) (see FIG. 6B). The second column further separated and purified the target diamondoids and then sent them into individual traps (traps 1–6). GC traps 2, 4 and 6 contained the selected tetramantanes (FIG. 6B).

Figure 7:
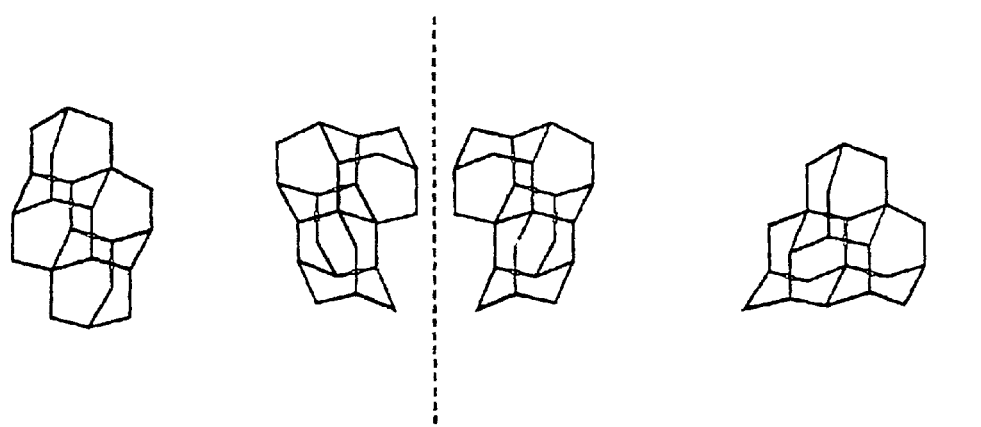
FIG. 7 illustrates the structures of the four-tetramantane isomers two of which are enantiomers.
Figure 8A:
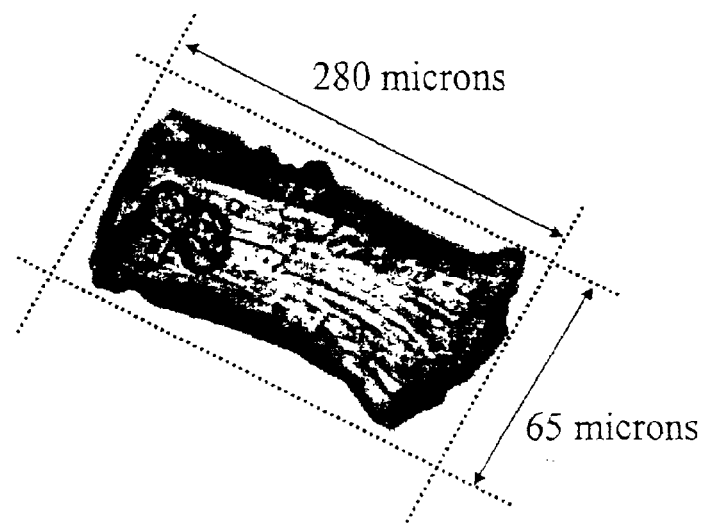
FIG. 8A was isolated from trap fraction 2, FIG. 8B was isolated from trap fraction 4, and FIG. 8C was isolated from trap fraction 6. Because the two enantiomeric tetramantanes have identical GC retentions times in FIG. 6, one of the crystals contains both enantiomers.
Figure 8B:
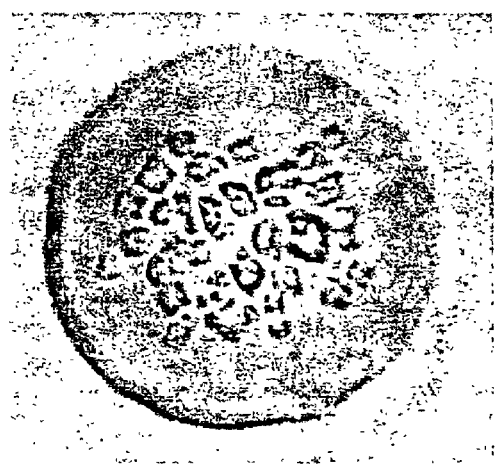
FIG. 8(A, B, C) illustrates photomicrographs of tetramantane crystals isolated from Feedstock A by preparative gas chromatography (FIG. 6).
Figure 8C:
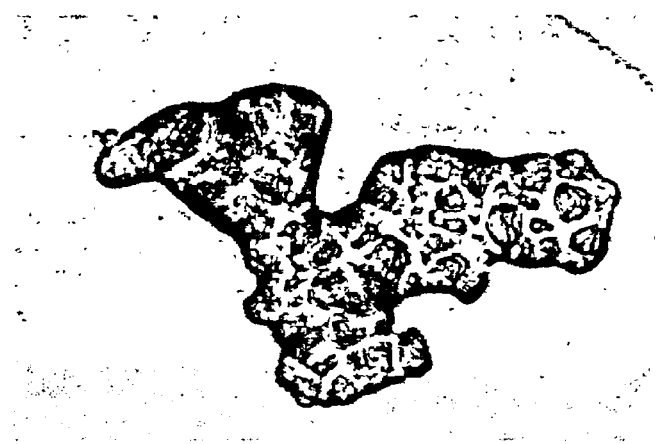

The highly concentrated diamondoids were then allowed to crystallize in the trap or from solution. Under the microscope at 30× magnification, crystals were visible in preparative GC trap fractions 2, 4, and 6 (see FIG. 6). Where concentrations were not high enough for crystallization to occur, further concentration by preparative GC was necessary. Structures of tetramantane isomers are shown in FIG. 7, including one, [123] using nomenclature of Balaban (Ref. #15) tetramantane as two enantiomeric forms. FIGS. 8A, B and C illustrates photomicrographs of tetramantane crystals isolated from Feedstock A from preparative GC trap fraction #2, fraction #4 and fraction #6 respectively.

After obtaining crystals of suitable size, material could be sent for structural determination using X-ray diffraction.

Figure 9:
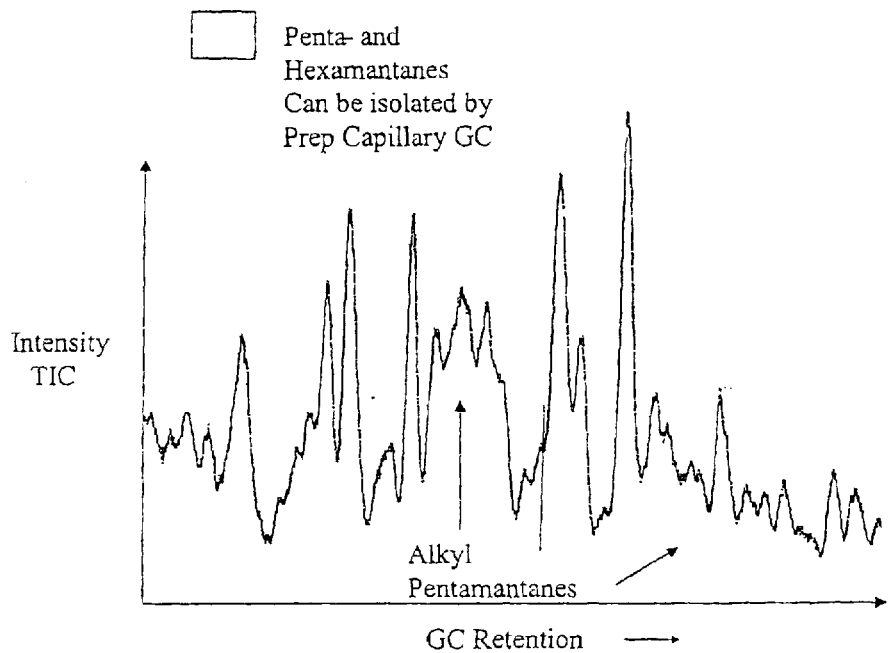
FIGS. 9–11 illustrate the GC retention time for a diamondoid condensate distilled and purified from Feedstock A, distillate fraction 38.
Figure 10:
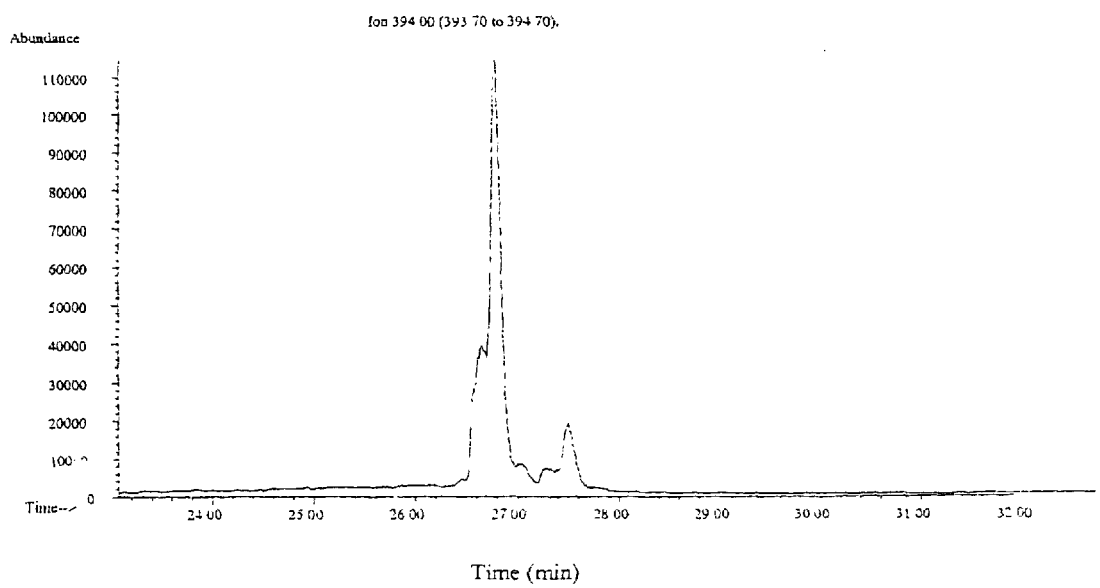
Figure 11:
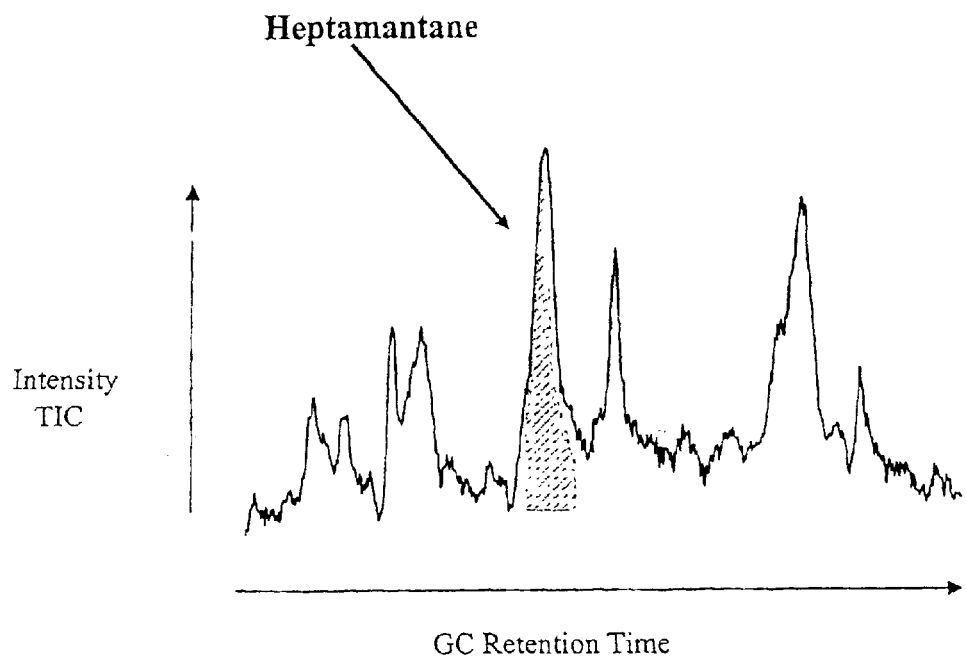

GC/MS (FIG. 9) showed the possible presence of target diamondoids higher than tetramantane (pentamantanes and hexamantanes) in distillate Fraction 38. Further GC/MS analyses of fraction 38 (Feedstock A) showed the presence of heptamantanes (FIGS. 10 and 11).

Example 4

Preparative GC of HPLC Fractions

For the heptamantanes, octamantanes and higher diamondoids, etc., it may be desirable to further fractionate the HPLC products obtained in Example 1, Step 7. This can be carried out using preparative capillary gas chromatography as described in Example 2, Step 7'.

Example 5

Pyrolysis of Feedstock B Distillate Fraction #5

Figure 13:
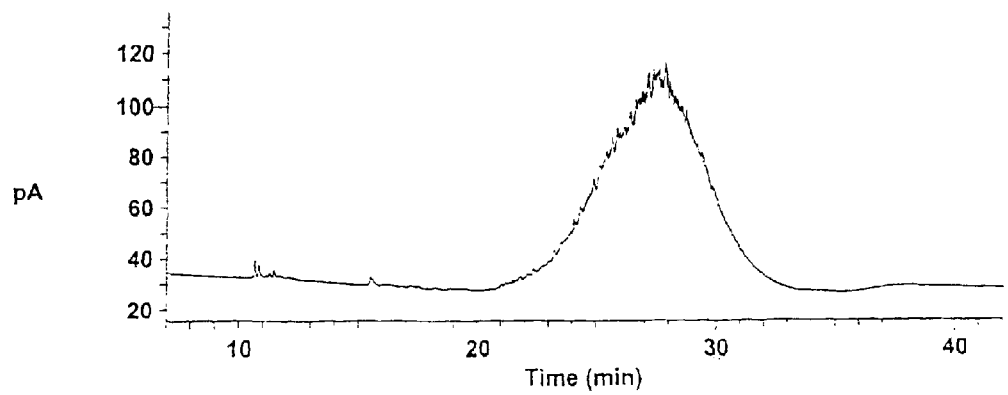
FIG. 13 illustrates the gas chromatogram of distillate Fraction #5 of Feedstock B atmospheric distillation 650° F.+ bottoms illustrated in FIG. 12 and exemplified in Example 1.
Figure 14:
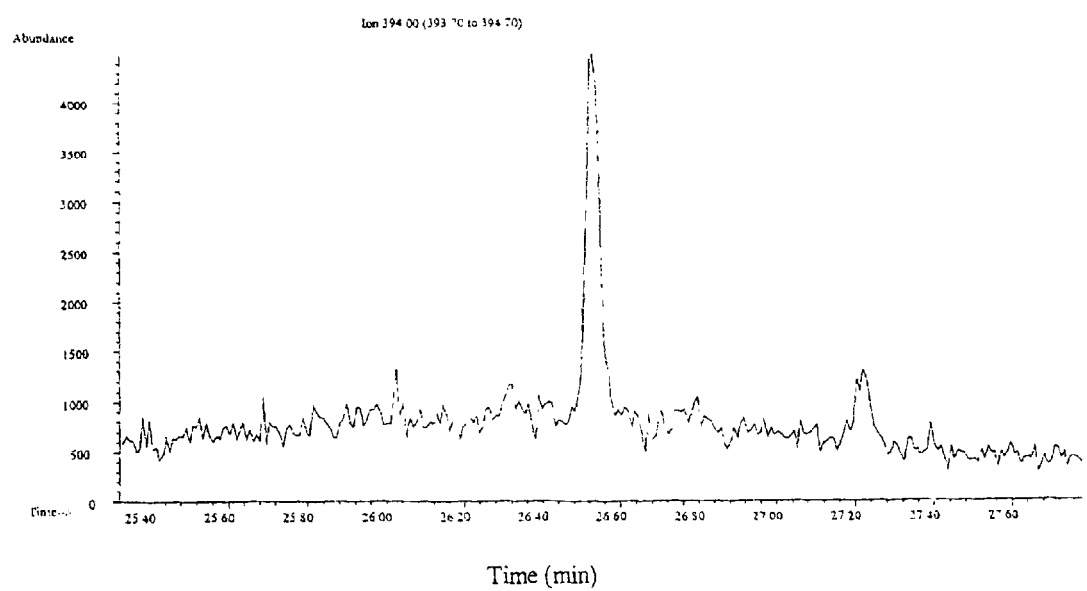
FIG. 14 illustrates the GC/MS selected ion chromatogram (m/z 394) showing the presence of the isomeric heptamantanes in the distillate Fraction #5 of Feedstock B atmospheric distillation 650° F.+ bottoms.

The method of Example 1, Step 5 was used to purify distillate fraction #5 obtained from Feedstock B– Atmospheric distillation 650° F.+ bottoms (Table 3A/B, FIG. 12 and FIG. 31) exploiting the great thermal stability of the higher diamondoid hydrocarbons relative to other crude oil components. FIG. 13 shows the GC profile of the distillate fraction #5 from Feedstock B– Atmospheric distillation 650° F.+ bottoms (see FIG. 12 and Table 3A&B). The GC-MS ion chromatogram in FIG. 14 shows the presence of target heptamantanes in this distillate Fraction #5.

Pyrolysis of Fraction #5 was conducted at 450° C. for 16.7 hrs. following the procedure of Example 1, Step 5. FIG. 21 illustrates the result and shows a gas chromatogram (on DB-17 equivalent GC column) of the starting material FIG. 21 (top) and pyrolysis product FIG. 21 (bottom).

Figure 22:
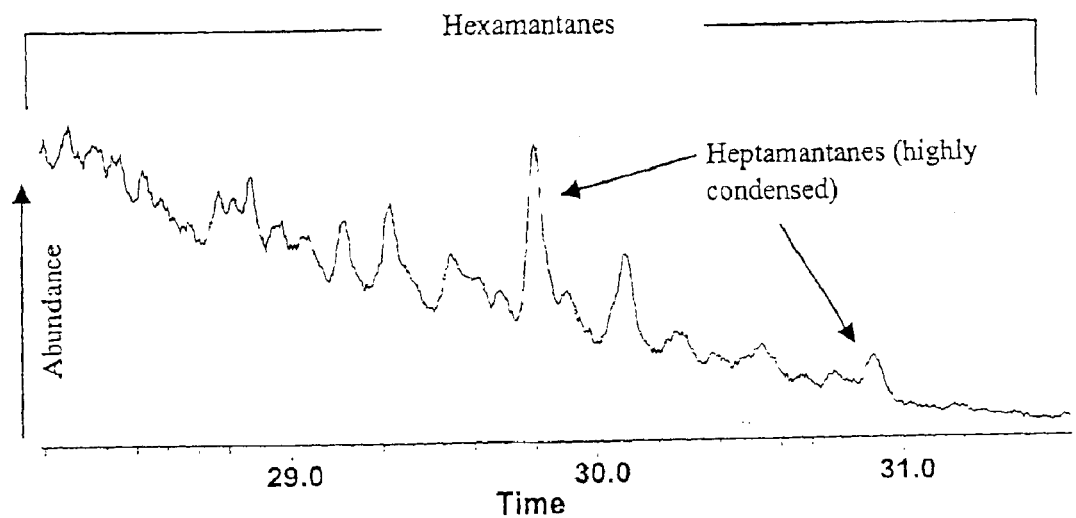
FIG. 22 illustrates an enlarged segment of the gas chromatogram of FIG. 21, from approximately 22 to 35 minutes, and the resulting hexamantanes and highly condensed heptamantanes available for isolation.

FIG. 22 shows an expansion of the 28.2 to 31.5 min. GC time range having the presence of hexamantanes and heptamantanes. This pyrolysis product was used in Example A.

Example 6

Removal of Nondiamondoids Using Pyrolysis During Isolation of Tetramantanes

Figure 15:
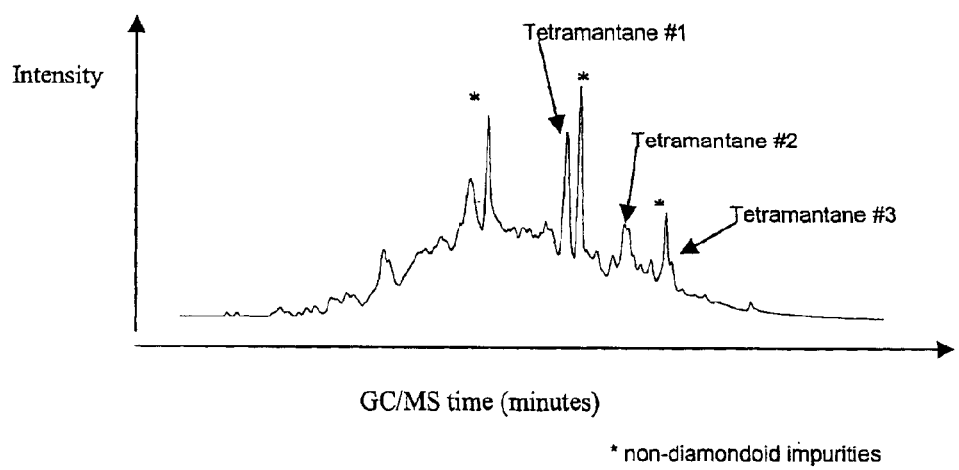
FIG. 15 illustrates the gas chromatogram of Feedstock B atmospheric distillation hold up fraction, exemplified in Example 1, which was used as feedstock in pyrolytic processing. The hold up fraction is the material recovered from the distillation column after distillation of Feedstock B at approximately 650° F.
Figure 16:
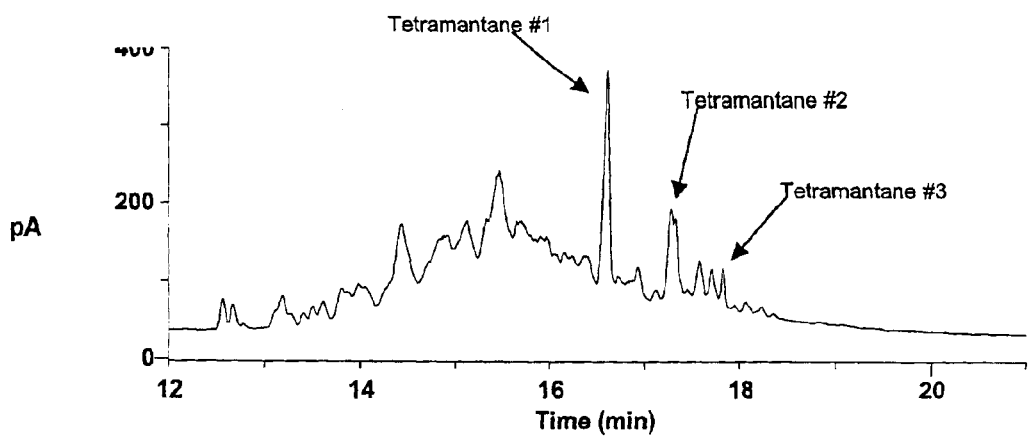
FIG. 16 illustrates the gas chromatogram of the pyrolytic product from the starting material in FIG. 15, i.e. the holdup fraction of Feedstock B atmospheric distillation 650° F.+ bottoms, showing the degradation of nondiamondoid components.

Example 1 was repeated with the conditions of Step 5 being changed. This method used a high-temperature reactor to pyrolyze and degrade a portion of the nondiamondoid components thereby enriching the diamondoids in the residue. FIGS. 15 and 16 illustrate this method and show gas chromatograms before pyrolysis (e.g. FIG. 15) and the resulting pyrolysis products (e.g. FIG. 16).

A PARR® reactor, from PARR INSTRUMENT COMPANY, Moline, Ill., was used to process the distillation column hold-up obtained after atmospheric distillation of a feedstream. For this example, Feedstock B 650° F.+ distillation holdup was used as a feedstock for pyrolysis. Pyrolysis was then conducted on this sample by heating the sample under vacuum in a vessel at 450° C. for 20.4 hours.

FIG. 15 shows the gas chromatogram of the distillation holdup and FIG. 16 shows the chromatograph of the products of the pyrolytic process. A comparison of FIGS. 15 and 16 show that the pyrolysis process has removed major nondiamondoid components leaving a residue enriched in diamondoids particularly tetramantanes.

Example 7

Isolations of Tetramantane Using HPLC

Figure 17:
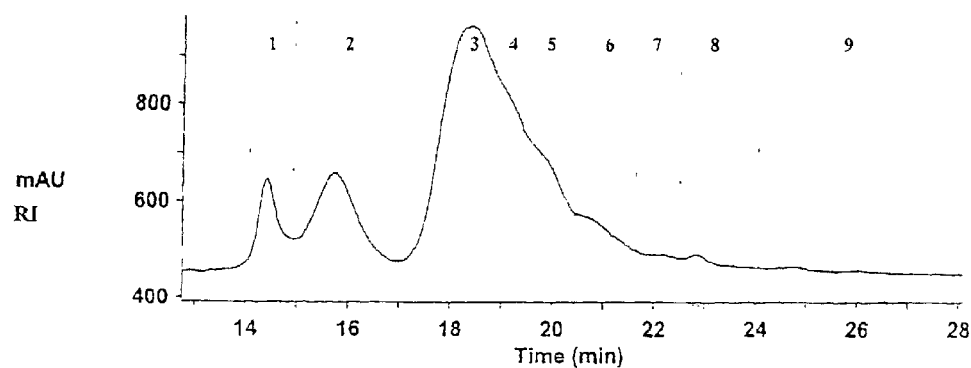
FIG. 17 illustrates the preparative ODS HPLC trace of Feedstock A gas condensate distillation fraction #32 showing fractions taken (1–9).

In addition to the pyrolysis method described above, HPLC was also shown to provide sufficient enrichments of some higher diamondoids to allow for their crystallization without pyrolysis. In some cases, reverse-phase HPLC with acetone as mobile phase can be used to effect this purification. A preparative HPLC run of Feedstock A, gas condensate distillate Fraction #32 was performed and the HPLC chromatogram recorded using a differential refractometer is shown in FIG. 17. Nine fractions where taken during the run as marked on FIG. 17. The HPLC columns used were two 25 cm×10 mm I.D. Vydac octadecyl silane (ODS) columns operated in series (Vydac columns are manufactured by The Separatations Group, Inc., CA, USA). A 20 microliter sample of a solution of Fraction #32 at 55 mg/mL in acetone was injected into the columns. The columns were setup using acetone at 2.00 mL/min at mobile phase.

Figure 36:
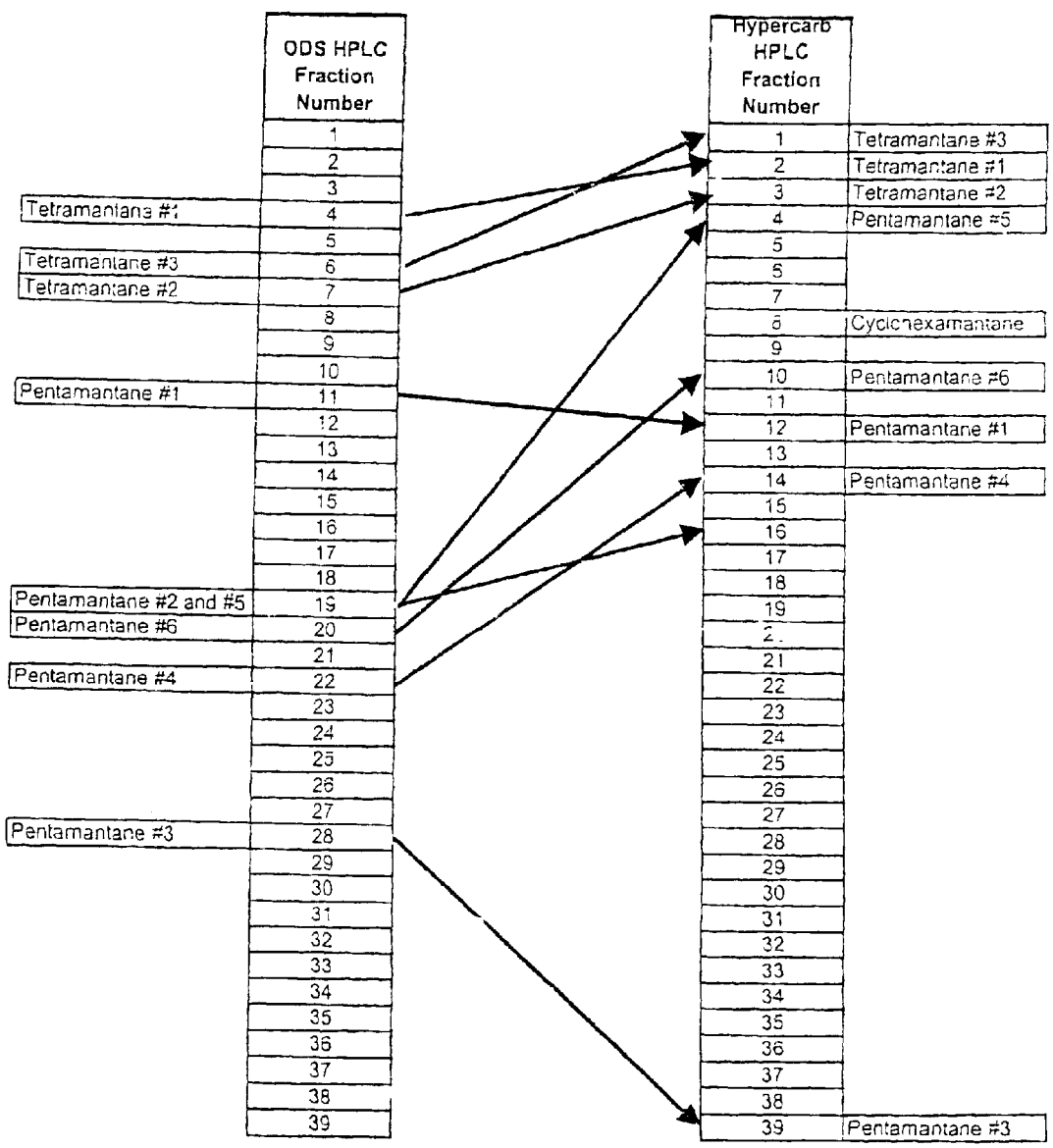
FIG. 36 shows the two-HPLC column strategy used to isolate individual tetramantanes and pentamantanes.

FIG. 36 illustrates the different HPLC elution orders of the tetramantanes on ODS and Hypercarb HPLC columns indicating how these two types of columns can be used together to isolate tetramantanes (and pentamantanes) in high purity.

Figure 18:
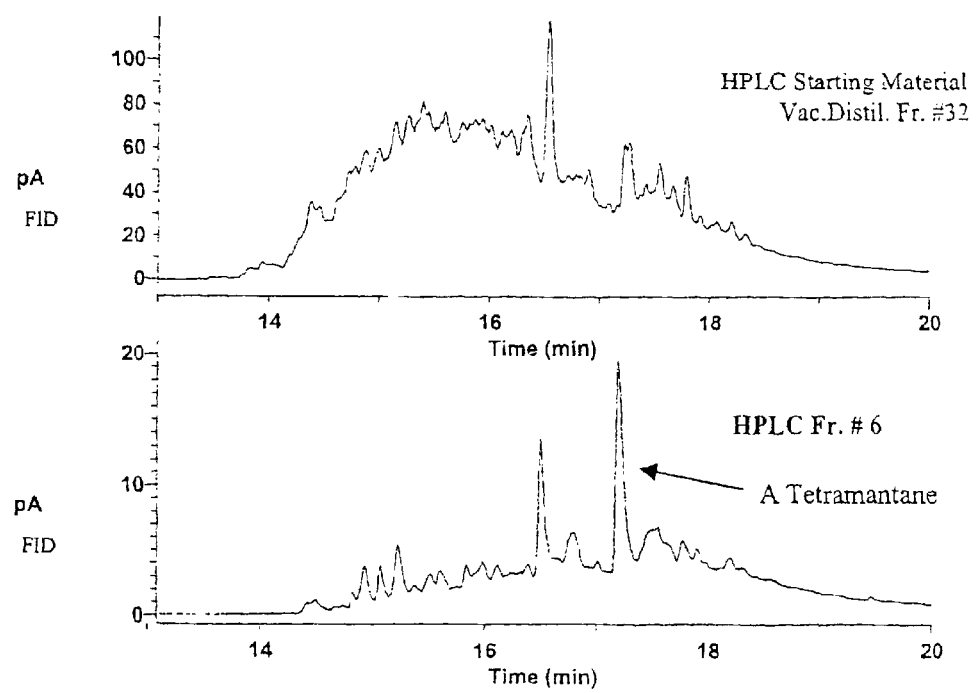
FIG. 18 illustrates gas chromatograms showing Feedstock A, distillate fraction #32, as compared to its HPLC fraction #6 indicated as shown in FIG. 17. HPLC fraction #6 shows significant enrichment in one of the tetramantane components.

FIG. 18 compares the gas chromatogram of the starting material (Feedstock A, distillation Fraction #32) and HPLC fraction #6, from FIG. 17. HPLC Fraction #6 is significantly enriched in a tetramantane (see GC/MS FIG. 19) and is approaching a concentration sufficient to bring about its crystallization.

Example 8

Comparison of Feedstocks and Isolation Procedures

This example illustrates isolation procedures to concentrate the higher diamondoids for further separations using different feedstocks.

Table 5 illustrates the concentration of higher diamondoids in select gas condensates rich in diamondoids compared to the concentration of higher diamondoids found in typical petroleum. Gas condensates from the Jurassic sandstone reservoirs of the Norphet Formation, Gulf Coast and in the LeDuc Formation, Canada have high initial diamondoid concentrations including higher diamondoids. Generally, a typical petroleum crude oil contains adamantanes present in a concentration of about 200 to 400 ppm. Of these higher diamondoids are about 0.5 weight percent of the entire amount of diamondoids in a typical crude oil.

TABLE 5

Comparison of Higher Diamondoid Concentration in Typical Petroleum vs. Select Gas Condensates Rich in Diamondoids

| Starting Material | Concentration of Higher Diamondoids (tetramantanes and higher) |
|---|---|
| Typical Petroleum | ~1 ppm or lower |
| Select Gas Condensates Rich in Diamondoids | 2500 ppm |

Other suitable feedstocks can also be found in refinery streams from crude oil processing. The concentrations of higher diamondoids in each refinery stream will depend on the type of crude oil and refinery operations including the distillation cut points, catalysts used and other processing operations (e.g. coking) that can increase higher diamondoid concentrations. These further processed refinery streams are identified as potential feedstocks for higher diamondoid isolations.

Table 6 illustrates the increases in higher diamondoid concentrations from initial isolation procedures of the feedstock. Such isolations can be atmospheric distillation, vacuum distillation, flash separation or other separation method known to those skilled in the art. Additionally, this treated product can further be coupled with another separation process such as pyrolytic processing.

TABLE 6

Comparison of Select Initial Isolation Procedures Used in Typical Petroleum and Diamondoid Enriched Condensate Isolations

| Initial Isolation Procedures for the Higher Diamondoids Fraction | Concentration of Higher Diamondoids (typical petroleum) | Concentration of Higher Diamondoids (gas condensate) |
|---|---|---|
| Atmospheric Distillation | ~1 ppm to ~100 ppm | >95 wt. |
| Atmospheric Distillation and Pyrolytic Processing, and Isolation of Saturated Hydrocarbons by Liquid Chromatography | >50 wt. % | >50 wt. % |

The concentration measurements outlined in Table 6 are dependent upon the weight percent atmospheric distillation residue (residue after a 650° F. (345° C.) distillation at atmospheric pressure). Higher diamondoids are present in the atmospheric distillation residue of crude oils, and the weight percent of atmospheric residual in a crude oil can vary from about 1 percent to less than about ~80 weight percent.

While Table 6 illustrates a combination of atmospheric distillation and pyrolytic processing, pyrolytic processing (thermal destruction of nondiamondoids) can be performed on un-distilled feed stock or vacuum distillate fractions. If so, the pyrolytically treated feedstock can then be subjected to removal of lower diamondoids.

Secondary isolation procedures could include either vacuum distillation used alone or in combination with liquid chromatography.

Fractionation of the atmospheric residue can also be performed prior to the pyrolytic processing.

Some overlap of higher diamondoid series occurs between distillation cuts, for example, the most structurally condensed hexamantane isomer distills at lower temperatures than other hexamantanes and is found in the pentamantane containing distillation fractions. Likewise, the most condensed isomers of the heptamantane series distills with the uncondensed hexamantanes, and so on. Furthermore, as the number of isomers and molecular weight series increase with each successive higher diamondoid series, boiling point distributions of series and isomers spread out with progressively more overlap of series occurring as molecular weights increase. Additionally, substituent groups on the isomers will effect the distillation fractions.

A tertiary isolation procedure can be used to further purify the products from the secondary isolation procedure or can be used in place of the secondary. For example, liquid chromatography can be use to remove aromatic hydrocarbons.

The tertiary isolation procedures comprises as examples, preparative Gas Chromatography and High Performance Liquid Chromatography. Other suitable separation technologies are known to those skilled in the art. These tertiary isolation procedures generate mixtures from which individual compounds can generally, but not always be crystalized for recovery. The highest purity values of Table 7 assume crystallization. Methods such as zone refining and vacuum sublimation can yield materials of much greater purities.

(polar) chromatographic column to further separate the target pentamantane. The material shunted to the second column was further cut and the product sent to a fraction collector, thus trapping two isolated pentamantanes.

The preparative gas chromatograph is computer assisted and can be operated in an automated mode.

Figure 23:
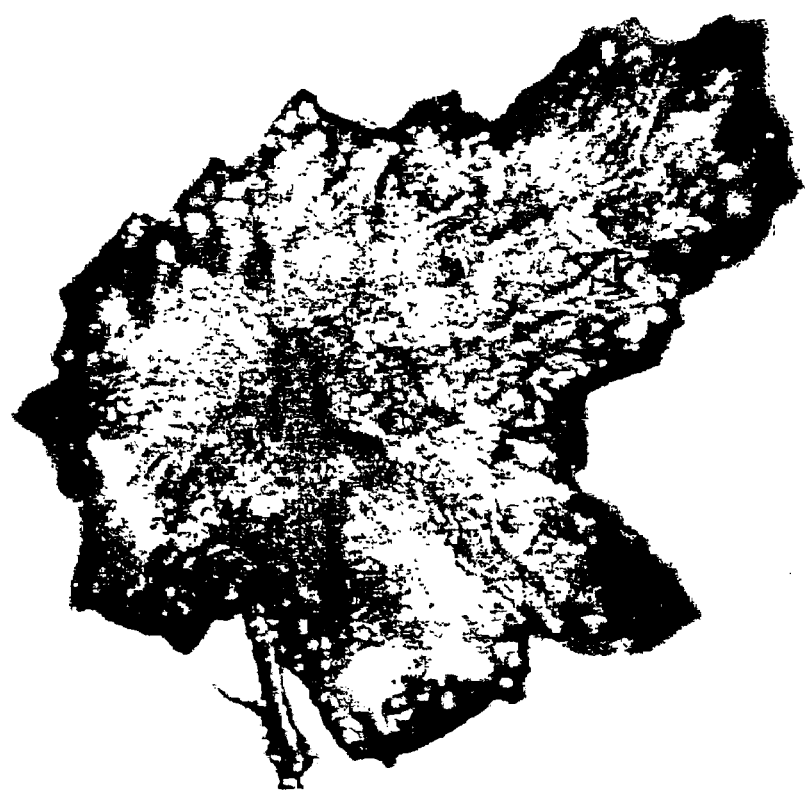
FIG. 23 illustrates a photomicrograph two co-crystallized pentamantane from Feedstock A.

When sufficient pentamantane was isolated in the collector trap, the trap was removed from the chromatograph and the two pentamantanes were dissolved in cyclohexane and crystallized. FIG. 23 shows a crystal approximately 250 micron in diameter that was dissolved in cyclohexane and recrystallized. It consists of two pentamantanes which co-crystallized. This procedure was also used on the pyrolysis product of Example 5 (cleaned-up using Example 1, Step 5) to isolate Pentamante #1 (the first pentamantane to elute in our GC/MS assay). FIG. 27 is a photomicrograph of Pentamantane #1 crystals and FIG. 27B and C are GC/MS TIC chromatogram and mass spectrum (showing high purity) isolated using this procedure.

Example 10

Heptamantanes, Octamantanes and Decamantanes in Pyrolysis Products

Evidence for the presence of these higher diamondoids in the cleaned-up pyrolysis product of Example 1, Step 6 is

TABLE 7

Purity of Individual Higher Diamondoids Obtained from Tertiary Isolation Procedures

| Tertiary Isolation Procedures of Individual Tetramantanes, Pentamantanes, Hexamantanes, etc., Fractions | Purity of Tetra-mantanes | Purity of Penta-mantanes | Purity of Hexa-mantanes | Purity of Hepta-mantanes | Purity of Octa-mantanes | Purity of Nona-Mantanes | Purity of Deca-mantanes |
|---|---|---|---|---|---|---|---|
| Preparative Gas Chromatography | >99.9 | >99.9 | >99.9 | >99.9 | >99.9 | >99.9 | >99.9 |
| High Performance Liquid Chromatography | >30–99.9 | >20–99.9 | >10–99.9 | >5–99.9 | >2–99.9 | >1–99.9 | 1>99.9 |

Example 9

Isolation of Pentamantanes by Preparative Capillary Gas Chromatography

A distillation fraction containing pentamantanes was processed using preparative capillary gas chromatography to exemplify the isolation of pentamantane.

The distillation fraction 38 was prepared by the distillation of gas condensate Feedstock A, and was treated by liquid chromatography (10% silver nitrate on silica gel) to remove all but the saturated hydrocarbons (FIG. 34). The preparative gas chromatographic fraction collector was set to collect material associated with a peak identified as a pentamantane isomer by gas chromatography mass spectroscopy (GC/MS) (FIG. 34, Step 2).

Figure 24:
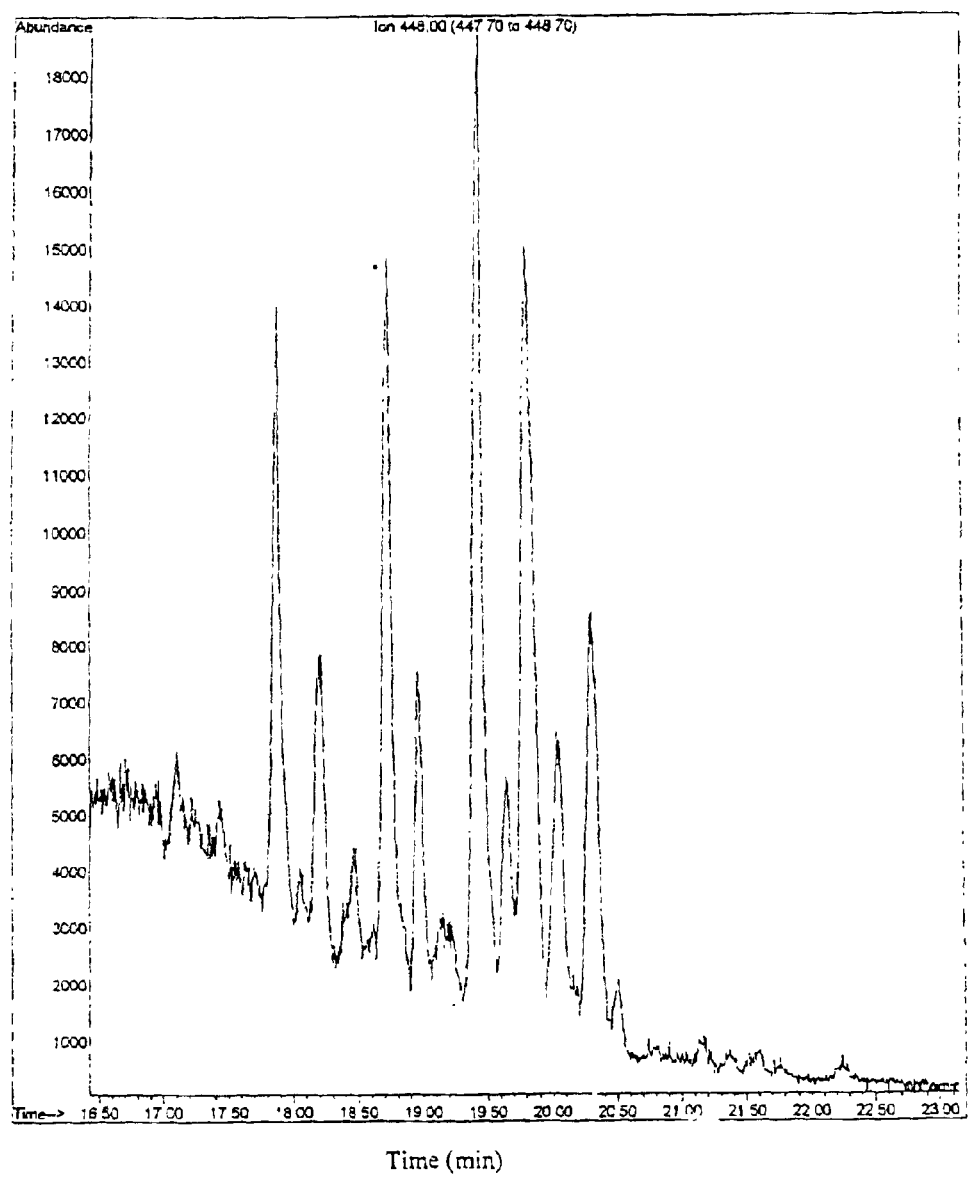
FIG. 24 illustrates a mass spectra of the distillate fraction #6, Feedstock B 650° F.+ distillation bottoms, pyrolysis product showing the presence of mol. wt. 448 heptamantanes purified therefrom.
Figure 25:
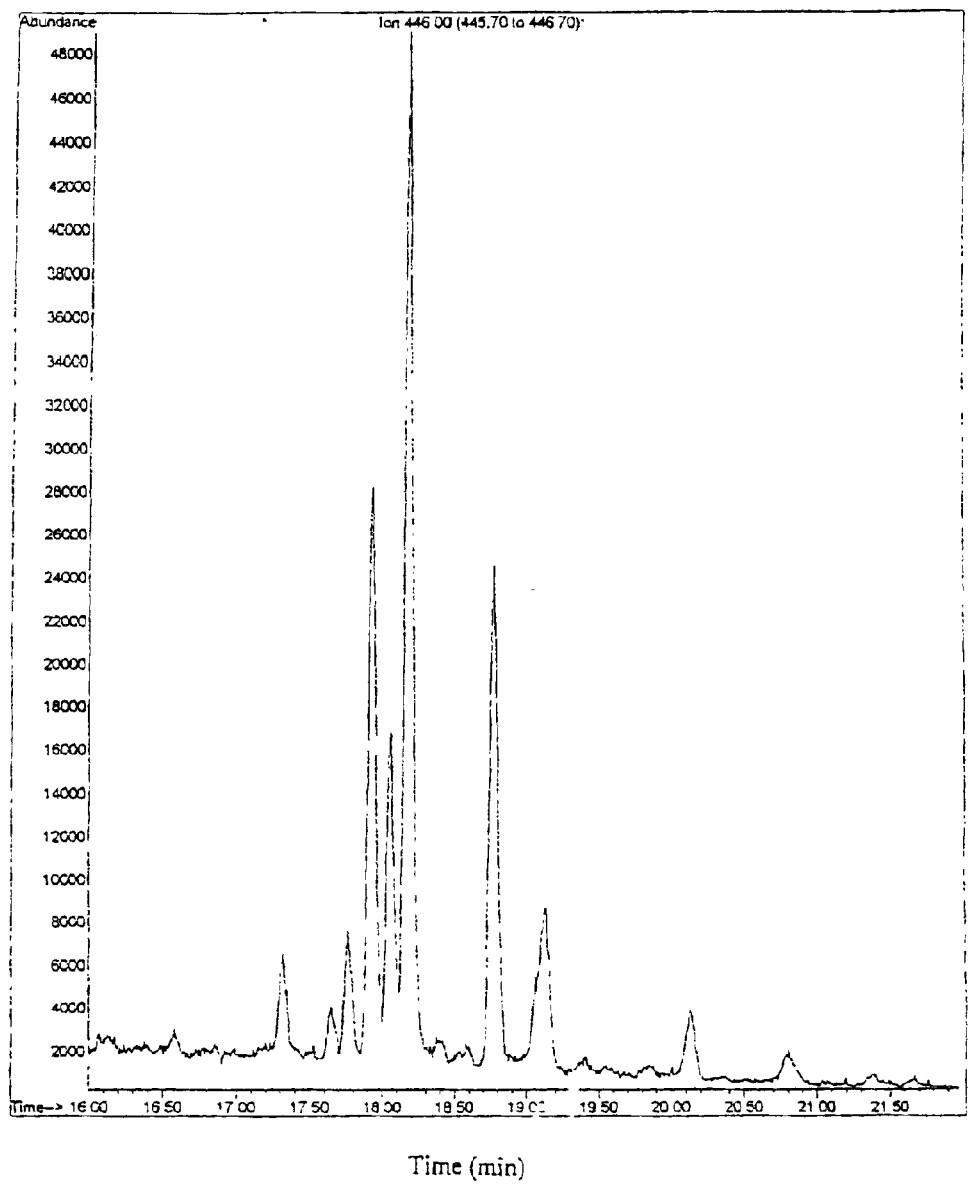
FIG. 25 illustrates a mass spectra of the distillate fraction #6, Feedstock B 650° F.+ distillation bottoms, pyrolysis product showing the presence of mol. wt. 446 octamantanes purified therefrom.
Figure 26:
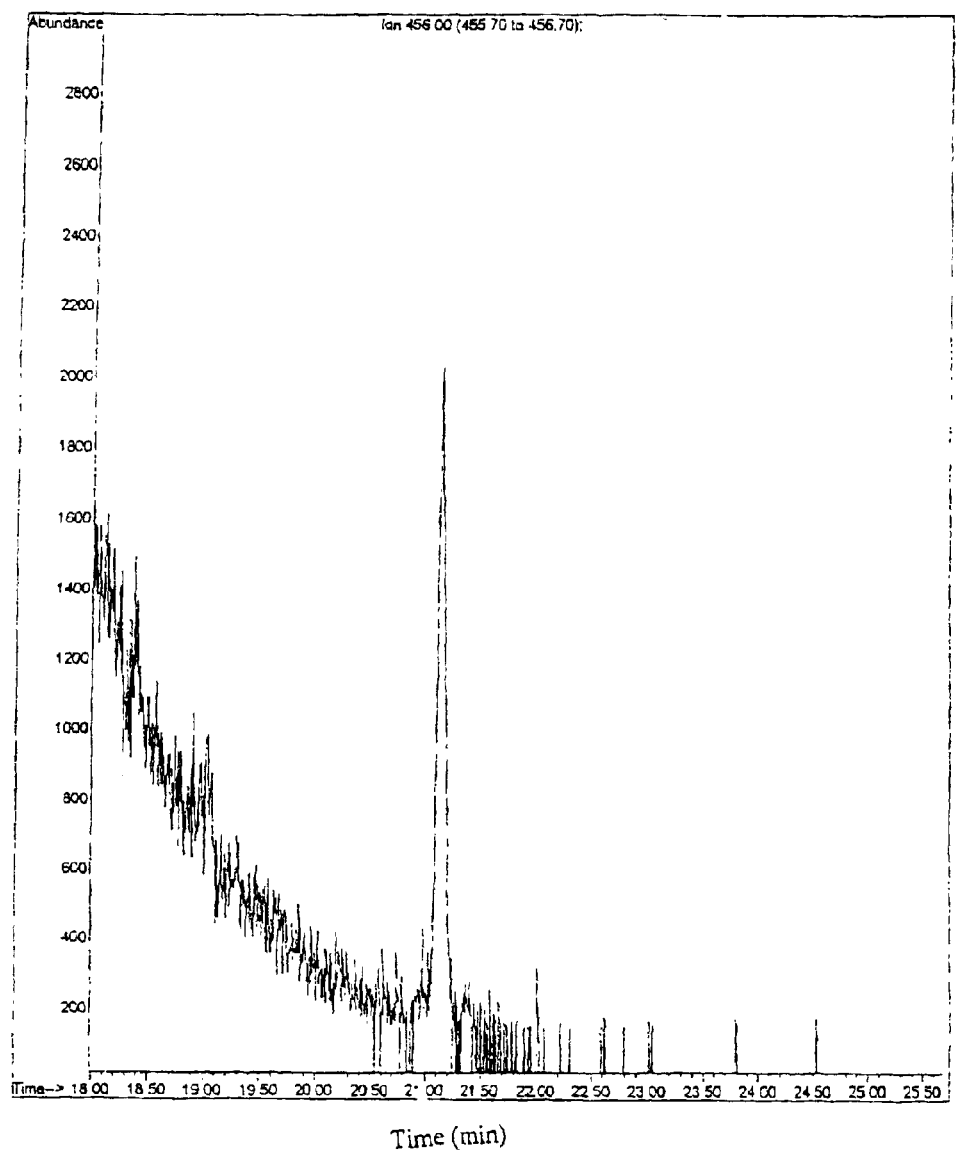
FIG. 26 illustrates a mass spectra of the distillate fraction #6, Feedstock B 650° F.+ distillation bottoms, pyrolysis product showing the presence of the most mol. wt. 456 decamantane purified therefrom.

The preparative gas chromatograph used two capillary columns to effect separation of the pentamantane. The distillate fraction sample in cyclohexane solution was injected (1 microliter) into a first gas chromatographic column with the inlet operating in splitless mode. The sample was separated utilizing the (nonpolar) gas chromatographic column and the chromatographic peak corresponding to the target pentamantane was shunted to a second shown in the ion chromatograms illustrated in FIGS. 24–26. Specifically, FIG. 24 shows the uncondensed heptamantanes at m/z 448; FIG. 25 shows the condensed octamantanes at m/z 446; FIG. 26 shows the highly condensed decamantane at m/z 456 in this material. GC/MS data illustrated in these FIGS. were used in GC/MS assays (Example 1, Step 2) in Examples 11, 12 and 14.

Example 11A

Isolation of Heptamantane Components by Preparative Capillary Gas Chromatography The eluent from the column chromatography (Step 6, FIG. 34) was analyzed by GC/MS to determine the GC retention times of heptamantanes. Individual heptamantane components with molecular weight 394 and 448 were assigned a number according to their elution order on our GC/MS assay (see FIG. 35A for representative assay values). Molecular weight 448 heptamantanes, the most abundant heptamantane family, were selected for convenience in this Example. Similar assays could be prepared for the other molecular weight heptamantanes.

A two-column preparative capillary gas chromatograph was then used to isolate heptamantanes from the distillate fractions cleaned-up by column chromatography. The cut times for the heptamantanes were set for the first preparative capillary GC column, methyl silicone DB-1 equivalent, using the retention times and patterns from GC/MS assay (from Step 2 above, FIG. 34).

The first column was used to concentrate the heptamantanes by taking cuts that were then sent to the second column. The second column, phenyl-methyl silicone a DB-17 equivalent, further separated and purified the heptamantane components and then was used to isolate peaks of interest and retain them in individual vials (traps 1–6). GC trap fraction 2 was collected and further processed for the separation of heptamantane #1. GC trap fraction 4 was collected and further processed for the separation of heptamantane #2. Subsequent GC/MS analysis of trap #2 material (FIGS. 29B and C) showed it to be heptamantane #1 based upon the earlier run GC/MS assay of step 4. Similarly, the GC analysis of trap #4 material showed it to be heptamantane #2. This procedure could be repeated to isolate the other heptamantane components.

The highly concentrated heptamantanes were then allowed to crystallize either directly in the trap or from solution. Under the microscope at 30× magnification, crystals were visible in preparative GC trap fraction 2 (see FIG. 29A). These crystals were perfectly clear and showed high refractive index. Crystals of heptamantane component #1 had never existed before this isolation. Where concentrations are not high enough for crystallization to occur, further concentration by preparative GC may be necessary. Crystals of heptamantane component #2 had never existed before this isolation.

After obtaining crystals of suitable size, heptamantane materials could be sent for structural determination using X-ray diffraction. Enantiomeric heptamantanes can undergo further separations to resolve their two components.

Example 11B

Purification of Single Heptamantane Components by HPLC

HPLC was also shown to provide sufficient enrichments of some heptamantanes to allow for their crystallization.

The HPLC columns used were the same as those given in the other examples (ODS and Hypercarb). A 500 microliter sample of a solution of the cut 7 pyrolysis product saturated hydrocarbon fraction (product of Step 6, FIG. 34) was injected into the ODS columns. Pyrolysis of Cut 7 used 25.8 g. heated at 450° C. for 16 hrs. Some of the ODS HPLC fractions reached the purity necessary for individual heptamantanes to crystallize (e.g., ODS HPLC fraction #45). Others, such as heptamantane #2 in ODS HPLC fraction #41, heptamantane #9 in ODS HPLC fraction #61, and heptamantane #10 in ODS HPLC fraction #87, required further separation on HPLC systems with different selectivities. Running the ODS fractions (FIG. 35B) on a Hypercarb column resulted in the purity necessary for individual heptamantane components to crystallize as shown for heptamantane component #1 in Hypercarb HPLC fraction #55 and heptamantane #2. The higher diamondoids in various HPLC fractions could be separated using further chromatographic techniques including preparative gas chromatography and additional HPLC runs using columns of different selectivity as outlined below. Additionally other techniques known in the crystallization art could be utilized including but not limited to fractional sublimation, progressive recrystallization or zone refining could be used to purify the heptamantanes.

By using similar methodology as above, i.e. fractionating heptamantane-containing ODS fractions using the Hypercarb or other suitable columns and collecting at corresponding elution times can lead to the isolation of the remaining heptamantanes. This is also true of the heptamantanes with molecular weights of 420 and 434, that are in much lower abundance in our feedstocks than heptamantane components showing molecular weights of 394 and 448. A heptamantane component of molecular weight 420 shows up in ODS HPLC fraction #61 with a very strong molecular ion in the mass spectrum for the m/z 420 component running at 16.71 min.

Example 11C

Isolation of Substituted Heptamantanes

Substituted heptamantanes including alkylheptamantanes also are present in Feedstock A and B. Alkylheptamantanes can be purified by removal of nondiamondoid impurities from feedstocks using pyrolysis as shown above. Certain alkylheptamantanes survive pyrolysis processing, as do the heptamantane components previously identified. Substituted heptamantanes including alkylheptamantanes can be isolated in high purity using a single HPLC separation. Monomethylated heptamantanes have a molecular weight of 408 (yielding a mass spectrometric molecular ion of m/z 408, and show a mass spectrometric loss of the methyl group giving the m/z 393 mass spectrometric fragment ion indicative of a heptamantane moiety.

Example 12A

Isolation of Octamantane Components

An octamantane-enriched fraction from Step 6 was subjected to reverse-phase HPLC. In some cases, reverse-phase HPLC with acetone as mobile phase can be used to effect this purification. A preparative ODS HPLC run of Feedstock B distillate cut 7 pyrolysis product saturated hydrocarbon fraction was performed and the HPLC chromatogram recorded using a differential refractometer. HPLC fractions were analyzed by GC/MS to determine octamantane HPLC elution times and monitor purity (see FIG. 35A for representative assay values). The HPLC columns used were the same ODS (FIG. 35B) and Hypercarb systems used in previous examples. A 500 microliter sample of an acetone solution of the cut 7 pyrolysis product saturated hydrocarbon fraction (25 mg) was injected into the ODS columns. While using this HPLC system, some octamantanes reached purity needed for individual octamantanes to crystallize. HPLC Fraction 63 yielded octamantane #3 and #5 together, which co-crystallized from the fraction.

For isolation in high purity of other octamantane components, multiple columns can be employed, e.g. Hypercarb.

Example 12B

Isolation of Substituted Octamantane Components

Alkyloctamantanes can be purified using methodologies described for non-alkylated octamantanes. ODS HPLC fraction 94 contains a methylated octamantane in high purity. Monomethylated octamantanes have a molecular weight of 460 (yielding a mass spectrometric molecular ion of m/z 460, and show a mass spectrometric loss of the methyl group giving the m/z 445 mass spectrometric fragment ion indicative of an octamantane moiety. Also, where more than one alkyloctamantane is present in an ODS or Hypercarb HPLC fraction, an additional HPLC separation of that fraction or preparative GC procedure (as in Example 3) can yield high purity alkyloctamantanes.

Example 13A

Isolation of Nonamantane Components

A preparative ODS HPLC run of Feedstock B distillate cut 7 pyrolysis product saturated hydrocarbon fraction was performed and the HPLC fractions were analyzed by GC/MS to determine nonamantane HPLC elution times and monitor purity. A 500 microliter sample of an acetone solution of the cut 7 pyrolysis product saturated hydrocarbon fraction (25 mg) was injected into the columns. The columns were set-up using acetone at 5.00 ml/min as a mobile phase carrier.

For isolation of nonamantane (FIG. 38), multiple HPLC columns can be employed. To illustrate this methodology, HPLC columns of different selectivities (ODS and Hypercarb, as described in previous examples) were used in succession to isolate a single nonamantane. From the ODS HPLC run, the nonamantane containing fractions 84–88 (FIG. 35B) were combined for further purification on a Hypercarb HPLC system.

We injected a 50 microliter sample of approximately 1 mg of ODS HPLC combined fraction (84–88) in methylene chloride onto two Hypercarb columns (4.6 mm I.D.×200 mm), operated in series using methylene chloride at 1.30 mL/min as mobile phase.

Nonamantane was isolated by a third HPLC run using the same Hypercarb stationary phase column but with a solvent consisting of methylene chloride/acetone (70:30 volume percent operating at 1.00 ml/min).

By using a similar methodology as above, i.e. fractionating nonamantane containing ODS HPLC fractions using columns with different selectivities, such as the Hypercarb or other suitable columns, we isolated a molecular weight 498 nonamantane in high purity (FIGS. 39 and 40). This method could be repeated to isolate the nonamantanes with molecular weights of 552, and the nonamantanes of molecular weights 538, 484 and 444, which respectively are in lower abundance in our feedstocks. Note that enantiomeric nonamantanes are not resolved in GS/MS, however these enantiomers can be isolated by chiral separation methods.

Example 13B

Isolation of Substituted Nonamantanes

Substituted nonamantanes also are present in Feedstock A and B. Alkylnonamantanes can be purified using methodologies described for non-alkylated nonamantanes. One type of monomethylated nonamantane has a molecular weight of 512 (yielding a mass spectrometric molecular ion of m/z 512, and show a mass spectrometric loss of the methyl group giving the m/z 497 mass spectrometric fragment ion indicative of a nonamantane moiety. More than one alkylnonamantane is present and these could be isolated using ODS or Hypercarb columns, an additional HPLC separation, or by preparative GC to yield high purity alkylnonamantanes

Example 14A

Isolation of Decamantane Components

A preparative ODS HPLC run of Feedstock B distillate cut 7 pyrolysis product saturated hydrocarbon fraction was performed and HPLC fractions were analyzed by GC/MS to determine decamantane HPLC elution times and monitor purity. The HPLC columns used were two 50 cm×20 mm I.D. Whatman octadecyl silane (ODS) columns operated in series. A 500 microliter sample of an acetone solution of the cut 7 pyrolysis product saturated hydrocarbon fraction (25 mg) was injected into the columns. The columns were set-up using acetone at 5.00 ml/min as a mobile phase carrier.

For isolation of decamantane components, multiple HPLC columns can be employed. To illustrate this methodology, HPLC columns of different selectivities were used in succession to isolate a single decamantane. The first HPLC system consisted of the same ODS columns described previously. From this HPLC run, the decamantane containing fractions 74–83 were combined for further purification on a second HPLC system. Five such runs were completed and all decamantane containing fractions from the runs were combined. This combined fraction contained a molecular weight 456 decamantane and various impurities.

To purify the combined HPLC fractions 74–83 from the ODS HPLC separation, we injected a 50 microliter sample of approximately 1 mg of ODS HPLC combined fraction in acetone/methylene chloride (70:30 volume percent) onto two Hypercarb columns, 4.6 mm I.D.×200 mm, operated in series using acetone/methylene chloride (70:30 volume percent) at 1.00 mL/min as mobile phase (@480 psi), and isolation (FIG. 39) and crystallization (FIG. 40) of decamantane was achieved.

By using a similar methodology as above, i.e. fractionating decamantane-containing ODS HPLC fractions using columns with different selectivities, such as the Hypercarb or other suitable columns, we isolated a molecular weight 456 decamantane in high purity (FIGS. 39 and 40). This method could be repeated to isolate the decamantanes with molecular weights of 496 as well as molecular weights 550 or 604, and the decamantanes of molecular weights 536, 576 and 590, which respectively are in lower abundance in our feedstocks. Note that enantiomeric decamantanes are not resolved in GS/MS, however these enantiomers can be isolated by chiral separation methods.

Example 14B

Isolation of Substituted Decamantanes

Substituted decamantanes also are present in Feedstock A and B. Alkyldecamantanes can be purified using methodologies described for non-alkylated decamantanes. One type of monomethylated decamantane has a molecular weight of 470 (yielding a mass spectrometric molecular ion of m/z 470). Also, where more than one alkyldecamantane is present in an ODS or Hypercarb HPLC fraction, an additional HPLC separation of that fraction or an alternative preparative GC procedure can yield high purity alkyldecamantanes.

Example 15

Isolation of Undecamantane Components

For isolation of undecamantane components in high purity, multiple HPLC columns can be employed. This methodology was demonstrated using decamantane with HPLC columns of different selectivities used in succession to isolate a single decamantane. An appropriate starting material, Feedstock B, distillation cut 7 pyrolysis product.

Undecamantane is concentrated in ODS HPLC fraction 100+ (FIG. 35B). This fraction could be purified on a Hypercarb HPLC using a system similar to that explained to isolate decamantane. This method could be repeated to isolate the undecamantanes with molecular weights of 656 and/or 602, as well as molecular weights 642, 628, 588, 548 or 534 which respectively are anticipated to be in lower abundance in our feedstocks.

What is claimed is:

1. A process which comprises:
   a. selecting a feedstock comprising recoverable amounts of a higher diamondoid component or components selected for recovery, nondiamondoid components and diamondoid components having a boiling point less than the lowest boiling point higher diamondoid component selected for recovery;
   b. removing from the feedstock a sufficient amount of components having a boiling point less than the lowest boiling point higher diamondoid component selected for recovery under conditions wherein recoverable amounts of the higher diamondoid component or components selected for recovery are retained in the treated feedstock; and
   c. thermally treating the feedstock recovered in b) above to pyrolyze at least a sufficient amount of nondiamondoid components therefrom to permit recovery of the selected higher diamondoid component or components from the thermally treated feedstock wherein the pyrolysis is conducted under conditions to provide a treated feedstock retaining recoverable amounts of the selected higher diamondoid component or components.

2. The process of claim 1 wherein the feedstock additionally comprises nondiamondoid components having a boiling point both below and above the lowest boiling point selected higher diamondoid component, and at least one lower diamondoid component.

3. A process of claim 1 additionally comprising the step d) recovering a composition enriched in one or more selected higher diamondoid components from said treated feedstock formed in b) above with one or more additional separation techniques selected from the group consisting of chromatographic techniques, thermal diffusion techniques, zone refining, progressive recrystallization and size separation techniques.

4. A process for recovering at least one selected higher diamondoid comprising selecting a feedstock containing a recoverable amount of the at least one selected higher diamondoid and recovering the at least one selected higher diamondoid from the feedstock by chromatography.

5. The process of claim 4 wherein the chromatography is gas chromatography.

6. The process of claim 4 wherein the chromatography is high pressure liquid chromatography.

7. The process of claim 6 wherein the liquid chromatography comprises chromatography on two liquid chromatography columns in sequence with the two columns having differing selectivities.

8. The process of claim 4 having an additional step and comprising selecting a feedstock containing a recoverable amount of the at least one selected higher diamondoid, treating the feedstock to produce a treated feedstock having an increased concentration of the at least one selected higher diamondoid, and recovering the at least one selected higher diamondoid from the treated feedstock by chromatography.

9. The process of claim 8 wherein the treating comprises fractionating the feedstock and wherein the treated feedstock comprises a feedstock fraction.

10. The process of claim 9 wherein the feedstock fraction is a distillation residue.

11. The process of claim 9 wherein the feedstock fraction is an overhead fraction.

12. The process of claim 8 wherein the treating comprises pyrolyzing and wherein the treated feedstock is a pyrolyzed feedstock.

13. The process of claim 8 wherein the treating comprises fractionating the feedstock to yield a feedstock fraction containing the at least one selected higher diamondoid and pyrolyzing the feedstock fraction and wherein the treated feedstock is the pyrolyzed feedstock fraction.

14. The process of claim 13 wherein the feedstock fraction is a distillation residue.

15. The process of claim 13 wherein the feedstock fraction is an overhead fraction.

16. The process of claim 8 wherein the treating comprises pyrolyzing the feedstock to yield a pyrolyzed feedstock and fractionating the pyrolyzed feedstock to yield a treated feedstock which is a pyrolyzed feedstock fraction containing the at least one selected higher diamondoid.

17. The process of claim 8 wherein the treating comprises removing aromatic and polar components by low pressure liquid chromatography.

18. A process for recovering at least one selected higher diamondoid comprising selecting a feedstock containing a recoverable amount of the at least one selected higher diamondoid in admixture with nondiamondoid materials, aromatics and polar components, distilling the feedstock to yield an overhead and a bottoms, the bottoms containing the at least one selected higher diamondoid, fractionating the bottoms to yield an overhead fraction containing the selected at least one higher diamondoid in admixture with nondiamondoid materials, aromatics and polar components, pyrolyzing the overhead fraction to reduce the concentration of nondiamondoid materials and to yield a pyrolyzed overhead fraction, treating the pyrolyzed overhead fraction by low pressure liquid chromatography to remove aromatics and polar components and yield a low pressure chromatographed pyrolyzed overhead fraction, and recovering the at least one selected higher diamondoid from the low pressure chromatographed pyrolyzed overhead fraction by final chromatography.

19. The process of claim 18 wherein the final chromatography is gas chromatography.

20. The process of claim 18 wherein the final chromatography is high pressure liquid chromatography.

21. The process of claim 20 wherein the high pressure liquid chromatography comprises chromatography on two liquid chromatography columns in sequence with the two columns having differing selectivities.

* * * * *